United States Patent
Surleraux et al.

(10) Patent No.: US 7,622,490 B2
(45) Date of Patent: Nov. 24, 2009

(54) BROADSPECTURM 2-AMINO-BENZOXAZOLE SULFONAMIDE HIV PROTEASE INHIBITORS

(75) Inventors: Dominique Louis Nestor Ghislain Surleraux, Machelen (BE); Sandrine Marie Helene Vendeville, Brussels (BE); Wim Gaston Verschueren, Berchem (BE); Marie-Pierre T. M. M. G De Bethune, Everberg (BE); Herman Augustinus De Kock, Arendonk (BE); Abdellah Tahri, Heverlee (BE)

(73) Assignee: Tibotec Pharmaceuticals, Ltd., Little Island, Co. Cork (IE)

( * ) Notice: Subject to any disclaimer, the term of this patent is extended or adjusted under 35 U.S.C. 154(b) by 66 days.

(21) Appl. No.: 10/474,485

(22) PCT Filed: May 10, 2002

(86) PCT No.: PCT/EP02/05212

§ 371 (c)(1),
(2), (4) Date: Oct. 9, 2003

(87) PCT Pub. No.: WO02/092595

PCT Pub. Date: Nov. 21, 2002

(65) Prior Publication Data

US 2004/0106661 A1 Jun. 3, 2004

(30) Foreign Application Priority Data

May 11, 2001 (EP) .................................. 01201732

(51) Int. Cl.
*A61K 31/423* (2006.01)
*C07D 263/58* (2006.01)
(52) U.S. Cl. ..................................... 514/375; 548/222
(58) Field of Classification Search ................. 548/222; 514/375
See application file for complete search history.

(56) References Cited

FOREIGN PATENT DOCUMENTS

| EP | 0445926 B1 | 9/1991 |
|---|---|---|
| EP | 0499299 B1 | 8/1992 |
| EP | 0721331 B1 | 7/1996 |
| WO | WO 9405263 A1 | 3/1994 |
| WO | WO-95/06030 A1 * | 3/1995 |
| WO | WO 9506030 A1 | 3/1995 |
| WO | WO 9622287 A1 | 7/1996 |
| WO | WO-96/28463 A1 * | 9/1996 |
| WO | WO 9628418 A1 | 9/1996 |
| WO | WO 9628463 A1 | 9/1996 |
| WO | WO 9628464 A1 | 9/1996 |
| WO | WO 9628465 A1 | 9/1996 |
| WO | WO 9718205 A1 | 5/1997 |
| WO | WO 9744014 A1 | 11/1997 |
| WO | WO 9842318 A1 | 10/1998 |
| WO | WO 9910326 A1 | 3/1999 |
| WO | WO 9933792 A2 | 7/1999 |
| WO | WO 9933793 A2 | 7/1999 |
| WO | WO 9933795 A1 | 7/1999 |
| WO | WO 9933815 A1 | 7/1999 |
| WO | WO 9967254 A2 | 12/1999 |
| WO | WO 9967417 A2 | 12/1999 |

OTHER PUBLICATIONS

Dunn et al., Genome Biology, Mar. 2002, 3(4), pp. 1-7.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Benet, L. et al., "Pharmacokinetics: The Dynamics of Drug Absorption, Distribution, and Elimination.", *Goodman and Gilman's The Pharmacological Basis of Therapeutics*, Eighth Edition, 1992, pp. 13-18, McGraw-Hill Inc.
Cross, et al., "Rules For The Nomenclature of Organic Chemistry, Section E: Stereochemistry." *Pure & Applied Chemistry*, 1976, pp. 13-30, vol. 45., Pergamon Press, Great Britain.
Hertogs, K. et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs.", *Antimicrobial Agents and Chemotherapy*, Feb. 1998, pp. 269-276, vol. 42, No. 2.

(Continued)

*Primary Examiner*—Laura L. Stockton

(57) ABSTRACT

The present invention concerns the compounds having the formula (I)

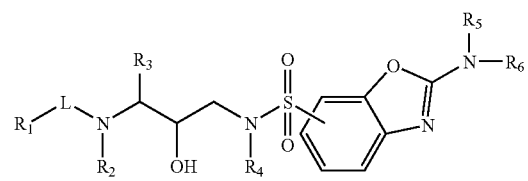

N-oxides, salts, stereoisomeric forms, racemic mixtures, prodrugs, esters and metabolites thereof, wherein $R_1$ and $R_8$ each are H, optionally substituted $C_{1-6}$alkyl, $C_{2-6}$alkenyl, $C_{3-7}$ cycloalkyl, aryl, $Het^1$, $Het^2$; $R_1$ may also be a radical of formula $(R_{11a}R_{11b})NC(R_{10a}R_{10b})CR_9$—; t is 0, 1 or 2; $R_2$ is H or $C_{1-6}$alkyl; L is —C(=O)—, —O—C(=O)—, —$NR_8$—C(=O)—, —$C_{1-6}$alkanediyl-C(=O)—, —$NR_8$—$C_{1-6}$alkanediyl-C(=O)—, —S(=O)$_2$—, —O—S(=O)$_2$—, —$NR_9$-S(=O)$_2$; $R_3$ is $C_{1-6}$alkyl, aryl, $C_{3-7}$cycloalkyl, $C_{3-7}$cycloalkyl$C_{1-4}$alkyl, or aryl$C_{1-4}$alkyl; $R_4$ is H, $C_{1-4}$alkylOC(=O), carboxyl, aminoC(=O), mono- or di($C_{1-4}$alkyl) aminoC(=O), $C_{3-7}$ cycloalkyl, $C_{2-6}$alkenyl, $C_{2-6}$alkynyl or optionally substituted $C_{1-6}$alkyl; $R_5$ and $R_6$ are H or $C_{1-6}$alkyl. It further relates to their use as broadspectrum HIV protease inhibitors, processes for their preparation as well as pharmaceutical compositions and diagnostic kits comprising them. It also concerns combinations thereof with another anti-retroviral agent, and to their use in assays as reference compounds or as reagents.

28 Claims, No Drawings

OTHER PUBLICATIONS

Augustijns, P. et al., "Drug absorption studies of prodrug esters using the Caco-2 model: evaluation of ester hydrolysis and transepithelial transport", International Journal of Pharmaceutics 166, (1998), pp. 45-53.

Pauwels, R. at al., "Rapid and automated tetrazolium-based colorimetric assay for the detection of anti-HIV compounds", Journal of Virological Methods, 20, (1988), pp. 309-321.

PCT Intl. Search Recport, PCT/EP2002/05212, Sep. 2, 2002.

* cited by examiner

BROADSPECTURM 2-AMINO-BENZOXAZOLE SULFONAMIDE HIV PROTEASE INHIBITORS

CROSS REFERENCE TO RELATED APPLICATIONS

This Application is a National Stage Application under 35 U.S.C. 371 of PCT/EP02/05212, filed May 10, 2002, which claims priority to European patent application EP 01201732.3, filed on May 11, 2001, all of which are incorporated herein by reference in their entirety.

The present invention relates to 2-amino-benzoxazole sulfonamides, their use as aspartic protease inhibitors, in particular as broadspectrum HIV protease inhibitors, processes for their preparation as well as pharmaceutical compositions and diagnostic kits comprising them. The present invention also concerns combinations of the present 2-aminobenzoxazole sulfonamides with another anti-retroviral agent. It further relates to their use in assays as reference compounds or as reagents.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-I and HIV-2. Hereinafter, HIV will be used to generically denote these viruses.

One of the critical pathways in a retroviral life cycle is the processing of polyprotein precursors by aspartic protease. For instance with the HIV virus the gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs), nucleotide reverse transcriptase inhibitors (NtRTIs) or other protease inhibitors. Despite the fact that these antiretrovirals are very useful, they have a common limitation, namely, the targeted enzymes in the HIV virus are able to mutate in such a way that the known drugs become less effective, or even ineffective against these mutant HIV viruses. Or, in other words, the HIV virus creates an ever increasing resistance against the available drugs.

Resistance of retroviruses, and in particular the HIV virus, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for retrovirus therapy, more particularly for AIDS therapy. The need in the art is particularly acute for compounds that are active not only on wild type HIV virus, but also on the increasingly more common resistant HIV viruses.

Known antiretrovirals, often administered in a combination therapy regimen, will eventually cause resistance as stated above. This often may force the physician to boost the plasma levels of the active drugs in order for said antiretrovirals to regain effectivity against the mutated HIV viruses. The consequence of which is a highly undesirable increase in pill burden. Boosting plasma levels may also lead to an increased risk of non-compliance with the prescribed therapy. Thus, it is not only important to have compounds showing activity for a wide range of HIV mutants, it is also important that there is little or no variance in the ratio between activity against mutant HIV virus and activity against wild type HIV virus (also defined as fold resistance or FR) over a broad range of mutant HIV strains. As such, a patient may remain on the same combination therapy regimen for a longer period of time since the chance that a mutant HIV virus will be sensitive to the active ingredients will be increased.

Finding compounds with a high potency on the wild type and on a wide variety of mutants is also of importance since the pill burden can be reduced if therapeutic levels are kept to a minimum. One way of reducing this pill burden is finding anti-HIV compounds with good bioavailability, i.e. a favorable pharmacokinetic and metabolic profile, such that the daily dose can be minimized and consequently also the number of pills to be taken.

Another important characteristic of a good anti-HIV compound is that plasma protein binding of the inhibitor has minimal or even no effect on its potency.

Thus, there is a high medical need for protease inhibitors that are able to combat a broad spectrum of mutants of the HIV virus with little variance in fold resistance, have a good bioavailability and experience little or no effect on their potency due to plasma protein binding.

Up until now, several protease inhibitors are on the market or are being developed.

One particular core structure (depicted below) has been disclosed in a number of references, such as, WO 95/06030, WO 96/22287, WO 96/28418, WO 96/28463, WO 96/28464, WO 96/28465 and WO 97/18205. The compounds disclosed therein are described as retroviral protease inhibitors.

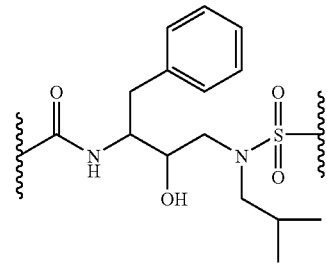

WO 99/67254 discloses 4-substituted-phenyl sulfonamides capable of inhibiting multi-drug resistant retroviral proteases.

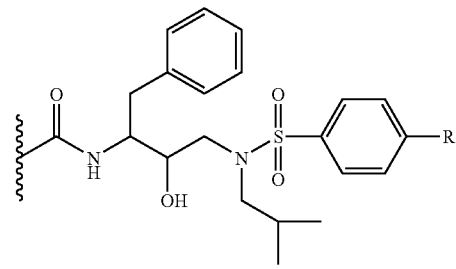

Surprisingly, the 2-amino-benzoxazole sulfonamides of the present invention are found to have a favorable pharmacological and pharmacokinetic profile. Not only are they active against wild-type HIV virus, but they also show a broadspectrum activity against various mutant HIV viruses exhibiting resistance against known protease inhibitors.

The present invention concerns 2-amino-benzoxazole protease inhibitors, having the formula

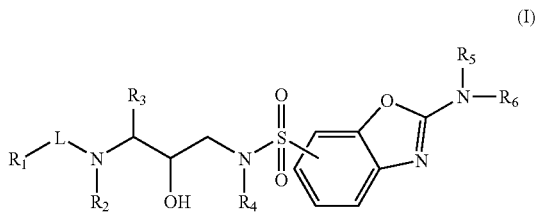

(I)

and N-oxides, salts, stereoisomeric forms, racemic mixtures, prodrugs, esters and metabolites thereof, wherein $R_1$ and $R_8$ are, each independently, hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^1$, Het$^1C_{1-6}$alkyl, Het$^2$, Het$^2C_{1-6}$alkyl;

$R_1$ may also be a radical of formula

(II)

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl; whereby $R_9$, $R_{10a}$ and the carbon atoms to which they are attached may also form a $C_{3-7}$cycloalkyl radical; when L is —O—$C_{1-6}$alkanediyl-C(=O)— or —NR$_8$—$C_{1-6}$alkanediyl-C(=O)—, then $R_9$ may also be oxo;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, Het$^1$ oxycarbonyl, Het$^2$ oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkylcarbonyl, $C_{3-7}$cycloalkyl-$C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkylcarbonyloxy, arylcarbonyloxy, aryloxycarbonyloxy, Het$^1$ carbonyl, Het$^1$ carbonyloxy, Het$^1C_{1-4}$alkyloxycarbonyl, Het$^2$carbonyloxy, Het$^2C_{1-4}$alkylcarbonyloxy, Het$^2C_{1-4}$alkyloxycarbonyl or $C_{1-4}$alkyl optionally substituted with aryl, aryloxy, Het$^2$ or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

$R_{11b}$ is hydrogen, $C_{3-7}$cycloalkyl, $C_{2-6}$alkenyl, $C_{2-6}$alkynyl, aryl, Het$^1$, Het$^2$ or $C_{1-4}$alkyl optionally substituted with halogen, hydroxy, $C_{1-4}$alkylS(=O)$_t$, aryl, $C_{3-7}$cycloalkyl, Het$^1$, Het$^2$, amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

whereby $R_{11b}$ may be linked to the remainder of the molecule via a sulfonyl group;

t is, each independently, zero, 1 or 2;

$R_2$ is hydrogen or $C_{1-6}$alkyl;

L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$ whereby either the C(=O) group or the S(=O)$_2$ group is attached to the NR$_2$ moiety; whereby the $C_{1-6}$alkanediyl moiety is optionally substituted with a substituent selected from hydroxy, aryl, Het$^1$, and Het$^2$;

$R_3$ is $C_{1-6}$alkyl, aryl, $C_{3-7}$cycloalkyl, $C_{3-7}$cycloalkyl$C_{1-4}$alkyl, or aryl$C_{1-4}$alkyl;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl, or $C_{1-6}$alkyl optionally substituted with one or more substituents each independently selected from aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(=O)$_t$, hydroxy, cyano, halogen and amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl-$C_{1-4}$alkyl, Het$^1$, Het$^2$, Het$^1C_{1-4}$alkyl and Het$^2C_{1-4}$alkyl;

$R_5$ is hydrogen or $C_{1-6}$alkyl;

$R_6$ is hydrogen or $C_{1-6}$alkyl.

A basic nitrogen occurring in the present compounds can be quaternized with any agent known to those of ordinary skill in the art including, for instance, lower alkyl halides, dialkyl sulfates, long chain halides and aralkyl halides.

Whenever the term "substituted" is used in defining the compounds of formula (1), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "$C_{1-4}$alkyl" as a group or part of a group defines straight and branched chained saturated hydrocarbon radicals having from 1 to 4 carbon atoms, such as, for example, methyl, ethyl, propyl, butyl and 2-methyl-propyl.

The term "$C_{1-6}$alkyl" as a group or part of a group defines straight and branched chained saturated hydrocarbon radicals having from 1 to 6 carbon atoms such as the groups defined for $C_{1-4}$alkyl and pentyl, hexyl, 2-methylbutyl, 3-methylpentyl and the like.

The term "$C_{1-6}$alkanediyl" as a group or part of a group defines bivalent straight and branched chained saturated hydrocarbon radicals having from 1 to 6 carbon atoms such as, for example, methylene, ethan-1,2-diyl, propan-1,3-diyl, propan-1,2-diyl, butan-1,4-diyl, pentan-1,5-diyl, hexan-1,6-diyl, 2-methylbutan-1,4-diyl, 3-methyl-pentan-1,5-diyl and the like.

The term "$C_{2-6}$alkenyl" as a group or part of a group defines straight and branched chained hydrocarbon radicals having from 2 to 6 carbon atoms containing at least one double bond such as, for example, ethenyl, propenyl, butenyl, pentenyl, hexenyl and the like.

The term "$C_{2-6}$alkynyl" as a group or part of a group defines straight and branched chained hydrocarbon radicals having from 2 to 6 carbon atoms containing at least one triple bond such as, for example, ethynyl, propynyl, butynyl, pentynyl, hexynyl and the like.

The term "$C_{3-7}$cycloalkyl" as a group or part of a group is generic to cyclopropyl, cyclobutyl, cyclopentyl, cyclohexyl or cycloheptyl.

The term "aryl" as a group or part of a group is meant to include phenyl and naphtyl which both may be optionally substituted with one or more substituents independently selected from $C_{1-6}$alkyl, optionally mono- or disubstituted amino$C_{1-6}$alkyl, $C_{1-6}$alkyloxy, halogen, hydroxy, hydroxy$C_{1-6}$ alkyl, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio, methylsulfonyl, and phenyl optionally substituted with one or more substituents, each independently selected from $C_{1-6}$alkyl, optionally mono- or disubstituted amino$C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl $C_{3-7}$cycloalkyl, Het$^1$, optionally mono- or disubstituted aminocarbonyl, methylthio and methylsulfonyl; whereby the optional substituents on any amino function are independently selected from $C_{1-6}$alkyl, $C_{1-6}$alkyloxy-A-, Het$^1$-A-, Het$^1C_{1-6}$alkyl, Het$^1C_{1-6}$alkyl-A-, Het$^1$oxy-A-, Het$^1$oxy$C_{1-4}$alkyl-A-, phenyl-A-, phenyl-oxy-A-, phenyloxy$C_{1-4}$alkyl-A-, phenyl$C_{1-6}$alkyl-A-, $C_{1-6}$alkyloxycarbonylamino-A-, amino-A-, amino$C_{1-6}$alkyl and amino$C_{1-6}$alkyl-A- whereby each of the amino groups may optionally be mono- or where possible di-substituted with $C_{1-4}$alkyl and whereby A is defined as $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$— whereby the point of attachment of A to the remainder of the molecule is the $C_{1-6}$alkanediyl group in those moieties containing said group.

An interesting subgroup in the definition of "aryl" as a group or part of a group includes phenyl and naphtyl which both may be optionally substituted with one or more substituents independently selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio, methylsulfonyl, and phenyl optionally substituted with one or more substituents selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio and methylsulfonyl; whereby the optional substituents on any amino function are independently selected from $C_{1-6}$alkyl, $C_{1-6}$alkyloxy-A-, Het$^1$-A-, Het$^1C_{1-6}$alkyl, Het$^1C_{1-6}$alkyl-A-, Het$^1$oxy-A-, Het$^1$oxy$C_{1-4}$alkyl-A-, phenyl-A-, phenyl-oxy-A-, phenyloxy$C_{1-4}$alkyl-A-, phenyl$C_{1-6}$alkyl-A-, $C_{1-6}$alkyloxycarbonyl-amino-A-, amino-A-, amino$C_{1-6}$alkyl and amino$C_{1-6}$alkyl-A- whereby each of the amino groups may optionally be mono- or where possible di-substituted with $C_{1-4}$alkyl and whereby A is as defined above.

The term "halo$C_1$alkyl" as a group or part of a group is defined as $C_{1-6}$alkyl substituted with one or more halogen atoms, preferably, chloro or fluoro atoms, more preferably fluoro atoms. Preferred halo$C_{1-6}$alkyl groups include for instance trifluoro-methyl and difluoromethyl.

The term "hydroxy$C_{1-6}$alkyl" as a group or part of a group is defined as $C_{1-6}$alkyl substituted with one or more hydroxy groups.

The term "Het$^1$" as a group or part of a group is defined as a saturated or partially unsaturated monocyclic, bicyclic or tricyclic heterocycle having 3 to 14 ring members, preferably 5 to 10 ring members and more preferably 5 to 8 ring members, which contains one or more heteroatom ring members, each independently selected from nitrogen, oxygen or sulfur, and which is optionally substituted on one or more carbon atoms by $C_{1-6}$alkyl, optionally mono- or disubstituted amino$C_{1-6}$alkyl, hydroxy$C_{1-6}$alkyl, $C_{1-6}$alkyloxy, halogen, hydroxy, oxo, optionally mono- or disubstituted, amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 14 ring members which contains one or more heteroatom ring members, each independently selected from nitrogen, oxygen or sulfur, and whereby the optional substituents on any amino function are independently selected from $C_{1-6}$alkyl, $C_{1-6}$alkyloxy-A-, Het$^2$-A-, Het$^2C_{1-6}$alkyl, Het$^2C_{1-6}$alkyl-A-, Het$^2$oxy-A-, Het$^2$oxy$C_{1-4}$alkyl-A-, aryl-A-, aryloxy-A-, aryloxy$C_{1-4}$alkyl-A-, aryl$C_{1-6}$alkyl-A-, $C_{1-6}$alkyloxycarbonylamino-A-, amino-A-, amino$C_{1-6}$alkyl and amino$C_{1-6}$alkyl-A- whereby each of the amino groups may optionally be mono- or where possible di-substituted with $C_{1-4}$alkyl and whereby A is as defined above.

An interesting subgroup in the definition of "Het$^1$" as a group or part of a group is defined as a saturated or partially unsaturated monocyclic, bicyclic or tricyclic hetero-cycle having preferably 3 to 12 ring members, more preferably 5 to 10 ring members and more preferably 5 to 8 ring members, which contains one or more heteroatom ring members selected from nitrogen, oxygen or sulfur and which is optionally substituted on one or more carbon atoms by $C_{1-6}$alkyl, $C_{1-6}$alkyloxy, halogen, hydroxy, oxo, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 12 ring members which contains one or more heteroatom ring members selected from nitrogen, oxygen or sulfur and whereby the optional substituents on any amino function are independently selected from $C_{1-6}$alkyl, $C_{1-6}$alkyloxy-A-, Het$^2$-A-, Het$^2C_{1-6}$alkyl, Het$^2C_{1-6}$alkyl-A-, Het$^2$-oxy-A-, Het$^2$oxy$C_{1-4}$alkyl-A-, aryl-A-, aryloxy-A-, aryloxy$C_{1-4}$alkyl-A-, aryl$C_{1-6}$alkyl-A-, $C_{1-6}$alkyloxycarbonylamino-A-, amino-A-, amino$C_{1-6}$alkyl and amino$C_{1-6}$alkyl-A- whereby each of the amino groups may optionally be mono- or where possible di-substituted with $C_{1-4}$alkyl and whereby A is as defined above.

The term "Het$^2$" as a group or part of a group is defined as an aromatic monocyclic, bicyclic or tricyclic heterocycle having 3 to 14 ring members, preferably 5 to 10 ring members and more preferably 5 to 6 ring members, which contains one or more heteroatom ring members each independently selected from nitrogen, oxygen or sulfur, and which is optionally substituted on one or more carbon atoms by $C_{1-6}$alkyl, optionally mono- or disubstituted amino$C_{1-6}$alkyl, hydroxy$C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 3 to 12 ring members; whereby the optional substituents on any amino function are independently selected from $C_{1-6}$alkyl, $C_{1-6}$alkyloxy-A-, Het$^1$-A-, Het$^1$C$_{1-6}$ alkyl, Het$^1$C$_{1-6}$alkyl-A-, Het$^1$oxy-A-, Het$^1$oxy-C$_{1-4}$alkyl-A-, aryl-A-, aryloxy-A-, aryloxyC$_{1-4}$alkyl-A-, arylC$_{1-6}$alkyl-A-, $C_{1-6}$alkyloxycarbonylamino-A-, amino-A-, aminoC$_{1-6}$alkyl and aminoC$_{1-6}$alkyl-A- whereby each of the amino groups may optionally be mono- or where possible di-substituted with $C_{1-4}$alkyl and whereby A is as defined above.

An interesting subgroup in the definition of "Het$^2$" as a group or part of a group is defined as an aromatic monocyclic, bicyclic or tricyclic heterocycle having preferably 3 to 12 ring members, more preferably 5 to 10 ring members and more preferably 5 to 6 ring members, which contains one or more heteroatom ring members selected from nitrogen, oxygen or sulfur and which is optionally substituted on one or more carbon atoms by $C_{1-6}$alkyl, $C_{1-6}$alkyloxy, halogen, hydroxy, optionally mono- or disubstituted amino, nitro, cyano, haloC$_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 3 to 12 ring members; whereby the optional substituents on any amino function are independently selected from $C_{1-6}$alkyl, $C_{1-6}$alkyloxy-A-, Het$^1$-A-, Het$^1$C$_{1-6}$alkyl, Het$^1$C$_{1-6}$alkyl-A-, Het$^1$oxy-A-, Het$^1$oxyC$_{1-4}$alkyl-A-, aryl-A-, aryloxy-A-, aryloxyC$_{1-4}$alkyl-A-, arylC$_{1-6}$alkyl-A-, $C_{1-6}$alkyloxycarbonylamino-A-, amino-A-, aminoC$_{1-6}$alkyl and aminoC$_{1-6}$alkyl-A- whereby each of the amino groups may optionally be mono- or where possible di-substituted with $C_{1-4}$alkyl and whereby A is as defined above.

As used herein, the term (=O) forms a carbonyl moiety with the carbon atom to which it is attached. The term (=O) forms a sulfoxide with the sulfur atom to which it is attached. The term (=O)$_2$ forms a sulfonyl with the sulfur atom to which it is attached.

As used herein, the term (=S) forms a thiocarbonyl moiety with the carbon atom to which it is attached.

As used herein before, the term "one or more" covers the possibility of all the available atoms, where appropriate, to be substituted, preferably, one, two or three.

When any variable (e.g. halogen or $C_{1-4}$alkyl) occurs more than one time in any constituent, each definition is independent.

The term "prodrug" as used throughout this text means the pharmacologically acceptable derivatives such as esters, amides and phosphates, such that the resulting in vivo biotransformation product of the derivative is the active drug as defined in the compounds of formula (1). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy group, for instance the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793 and WO 99/33792 all incorporated herein by reference.

Prodrugs are characterized by excellent aqueous solubility, increased bioavailability and are readily metabolized into the active inhibitors in vivo.

For therapeutic use, the salts of the compounds of formula (I) are those wherein the counterion is pharmaceutically or physiologically acceptable. However, salts having a pharmaceutically unacceptable counterion may also find use, for example, in the preparation or purification of a pharmaceutically acceptable compound of formula (I).

All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms which the compounds of the present invention are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods which may advantageously be employed are, for example, selective crystallization and chromatography, e.g. column chromatography.

It is clear to a person skilled in the art that the compounds of formula (I) contain at least one asymmetric center and thus may exist as different stereoisomeric forms. This asymmetric center is indicated with an asterisk (*) in the figure below.

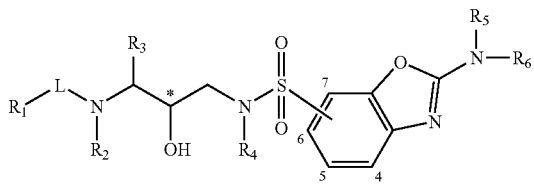

The absolute configuration of each asymmetric center that may be present in the compounds of formula (I) may be indicated by the stereochemical descriptors R and S, this R and S notation corresponding to the rules described in Pure Appl. Chem. 1976, 45, 11-30. The carbon atom marked with the asterisk (*) preferably has the R configuration.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", or "the present compounds" or similar term is meant to include the compounds of general formula (I), their N-oxides, salts, stereoisomeric forms, racemic mixtures, prodrugs, esters and metabolites, as well as their quaternized nitrogen analogues.

An interesting group of compounds are those of formula (I) wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbohyl, $C_{3-7}$cycloalkyl, $C_{2-6}$alkenyl, $C_{2-6}$alkynyl or $C_{1-4}$alkyl optionally substituted with aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl; whereby $R_9$, $R_{10a}$ and the carbon atoms to which they are attached may also form a $C_{3-7}$cycloalkyl radical;

$R_{11b}$ is hydrogen, $C_{3-7}$cycloalkyl, $C_{2-6}$alkenyl, $C_{2-6}$alkynyl, aryl, $Het^1$, $Het^2$ or $C_{1-4}$alkyl optionally substituted with halogen, hydroxy, $C_{1-4}$alkylS(=O)$_t$, aryl, $C_{3-7}$cycloalkyl, $Het^1$, $Het^2$, amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

whereby $R_{11b}$ may be linked to the remainder of the molecule via a sulfonyl group;

t is zero, 1 or 2;

L is —C(=O)—, —O—C(=O)—, —NR$_8$—C(=O)—, —O—C$_{1-6}$alkanediyl-C(=O)—, —NR$_8$—C$_{1-6}$alkanediyl-C(=O)—, —S(=O)$_2$—, —O—S(=O)$_2$—, —NR$_8$—S(=O)$_2$ whereby either the C(=O) group or the S(=O)$_2$ group is attached to the NR$_2$ moiety;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl, or $C_{1-6}$alkyl optionally substituted with one or more substituents selected from aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(=O)$_t$, hydroxy, cyano, halogen and amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl-$C_{1-4}$alkyl, $Het^1$, $Het^2$, $Het^1C_{1-4}$alkyl and $Het^2C_{1-4}$alkyl;

A particular group of compounds are those compounds of formula (I) wherein one or more of the following restrictions apply:

$R_1$ is hydrogen, $Het^1$, $Het^2$, aryl, $Het^1C_{1-6}$alkyl, $Het^2C_{1-6}$alkyl, aryl$C_{1-6}$alkyl, more in particular, $R_1$ is a saturated or partially unsaturated monocyclic or bicyclic heterocycle having 5 to 8 ring members, which contains one or more heteroatom ring members selected from nitrogen, oxygen or sulfur and which is optionally substituted, or phenyl optionally substituted with one or more substituients;

$R_2$ is hydrogen;

L is —C(=O)—, —O—C(=O)—, —O—C$_{1-6}$alkanediyl-C(=O)—, more in particular, L is —O—C(=O)— or —O—C$_{1-6}$alkanediyl-C(=O)—, whereby in each case the C(=O) group is attached to the NR$_2$ moiety;

$R_3$ is aryl$C_{1-4}$alkyl, in particular, arylmethyl, more in particular phenylmethyl;

$R_4$ is optionally substituted $C_{1-6}$alkyl, in particular unsubstituted $C_{1-6}$alkyl or $C_{1-6}$alkyl optionally substituted with one or more substituents selected from aryl, $Het^1$, $Het^2$, $C_{3-7}$cycloalkyl and amino optionally mono- or disubstituted where the substituents are selected from $C_{1-4}$alkyl; aryl, $Het^1$ and $Het^2$;

$R_5$ is hydrogen or methyl;

$R_6$ is hydrogen or methyl.

A special group of compounds are those compounds of formula (I) wherein $R_1$-L is $Het^1$-O—C(=O), $Het^2$-$C_{1-6}$alkanediyl-O—C(=O), aryl-O—$C_{1-6}$alkanediyl-C(=O) or aryl-C(=O).

Also a special group of compounds are those compounds of formula (I) wherein $NR_5S_6$ is amino, monomethylamino or dimethylamino.

Of particular interest are those compounds of formula (I) wherein $R_1$ is hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, $Het^1$, $Het^1C_{1-6}$alkyl, $Het^2$, $Het^2C_{1-6}$alkyl, in particular, $R_1$ is hydrogen, $C_{1-6}$alkyl, $C_{2-6}$alkenyl aryl$C_{1-6}$alkyl, $C_{3-7}$cycloalkyl, $C_{3-7}$cycloalkyl$C_{1-6}$alkyl, aryl, $Het^1$, $Het^2C_{1-6}$alkyl.

An interesting group of compounds are those compounds of formula (I) wherein $R_1$ is hydrogen, $C_{1-6}$alkyl, $C_{2-6}$alkenyl, aryl$C_{1-6}$alkyl, $C_{3-7}$cycloalkyl, $C_{3-7}$cycloalky-$C_{1-6}$alkyl, aryl, $Het^1$, $Het^1C_{1-6}$alkyl, $Het^2$, $Het^2C_{1-6}$alkyl; wherein $Het^1$ is a saturated or partially unsaturated monocyclic heterocycle having 5 or 6 ring members, which contains one or more heteroatom ring members selected from nitrogen, oxygen or sulfur and which is optionally substituted on one or more carbon atoms.

Another interesting group of compounds are those compounds of formula (I) wherein L is —O—$C_{1-6}$alkanediyl-C(=O)—.

A preferred group of compounds are those compounds where the sulfonamide group is attached to the benzoxazole group in the 6-position.

A suitable group of compounds are those compounds of formula (I) wherein $R_1$ is aryl or aryl$C_{1-6}$alkyl; in particular the aryl moiety of the $R_1$ definition is further substituted on one or more ring members, whereby each substituent is independently selected from $C_{1-4}$alkyl, hydroxy, halogen, optionally mono- or disubstituted amino, optionally mono- or disubstituted amino$C_{1-4}$alkyl, nitro and cyanogen; preferably the substituent is selected from methyl, ethyl, chlorine, iodine, bromine, hydroxy and cyanogen, in particular the aryl moiety contains 6 to 12 ring members, more in particular the aryl moiety in the definition of $R_1$ contains 6 ring members.

A suitable group of compounds are those compounds of formula (I) wherein $R_1$ is $Het^2$ or $Het^2C_{1-6}$alkyl, wherein the $Het^2$ in the definition of $R_1$ contains one or more heteroatoms each independently selected from nitrogen, oxygen and sulfur; in particular the $Het^2$ moiety of the $R_1$ definition is further substituted on one or more ring members, whereby each substituent is independently selected from $C_{1-4}$alkyl, hydroxy, halogen, optionally mono- or disubstituted amino and cyanogen; preferably the substituent is selected from methyl, ethyl, chlorine, iodine, bromine, hydroxy, amino and cyanogen.

Another group of compounds are those of formula (I) wherein $R_1$ is $Het^2$ or $Het^2C_{1-6}$alkyl, L is —C(=O)—, —O—C(=O)—, —O—$C_{1-6}$alkanediyl-C(=O)—; in particular the $Het^2$ moiety in the definition of $R_1$ is an aromatic heterocycle having 5 or 6 ring members, which contain one or more heteroatom ring members each independently selected from nitrogen, oxygen or sulfur, more in particular the $Het^2$ moiety is an aromatic heterocycle having 5 or 6 ring members, which contain two or more heteroatom ring members each independently selected from nitrogen, oxygen or sulfur.

A suitable group of compounds are those compounds of formula (1) wherein $R_1$ is $Het^1$ or $Het^1C_{1-6}$alkyl, wherein $Het^1$ in the definition of $R_1$ contains one or more heteroatoms each independently selected from nitrogen, oxygen and sulfur; in particular the $Het^1$ moiety of the definition of $R_1$ is further substituted on one or more ring members, whereby each substituent is independently selected from $C_{1-4}$alkyl, hydroxy, halogen, optionally mono- or disubstituted amino and cyanogen; preferably the substituent is selected from methyl, ethyl, chlorine, iodine, bromine, hydroxy, amino and cyanogen.

A suitable group of compounds are those compounds of formula (I) wherein $R_1$ is $Het^1C_{1-6}$alkyl, $Het^1$, wherein said $Het^1$ in the definition of $R_1$ is monocyclic having 5 or 6 ring members, wherein the $Het^1$ contains one or more heteroatoms each independently selected from nitrogen, oxygen and sulfur; in particular the $Het^1$ moiety of the $R_1$ definition is further substituted on one or more carbon atoms, whereby each substituent is independently selected from $C_{1-4}$alkyl, hydroxy, halogen, optionally mono- or disubstituted amino and cyanogen; preferably the substituent is selected from methyl, ethyl, chlorine, iodine, bromine, hydroxy, amino and cyanogen.

A suitable group of compounds are those compounds of formula (I) wherein $R_1$ is $Het^1$, wherein said $Het^1$ is bicyclic having 8 to 10 ring members, wherein the $Het^1$ contains one or more heteroatoms each independently selected from nitrogen, oxygen and sulfur; in particular the $Het^1$ moiety of the $R_1$ definition is further substituted on one or more carbon atoms, whereby each substituent is independently selected from $C_{1-4}$alkyl, hydroxy, halogen, optionally, mono- or diisubstituted amino and cyanogen; preferably the substituent is selected from methyl, ethyl, chlorine, iodine, bromine, hydroxy, amino and cyanogens, in particular the $Het^1$ moiety contains 2 or more heteroatoms selected from nitrogen, sulfur and oxygen.

A suitable group of compounds are those compounds of formula (I) wherein $R_1$ is $Het^1$, wherein said $Het^1$ is a satured bicyclic group having 5 to 10 ring members, wherein the $Het^1$ contains one or more heteroatoms each independently selected from nitrogen, oxygen and sulfur; in particular the $Het^1$ moiety of the $R_1$ definition is further substituted on one or more carbon atoms, whereby each substituent is independently selected from $C_{1-4}$alkyl, hydroxy, halogen, optionally mono- or disubstituted amino and cyanogen; preferably the substituent is selected from methyl, ethyl, chlorine, iodine, bromine, hydroxy, amino and cyanogens; in particular $Het^1$ contains 5 to 8 ring members; in particular the $Het^1$ moiety has 6 to 8 ring members wherein $Het^1$ contains 2 or more heteroatoms selected from nitrogen, sulfur and oxygen.

An interesting group of compounds are those compounds of formula (I) wherein $R_1$ is G or G-$C_{1-6}$alkyl, wherein G is selected from thiazolyl, imidazolyl, oxazolyl, oxadiazolyl, dioxazolyl, pyrazolyl, pyrazinyl, imidazolinionyl, quinolinyl, isoquinolinyl, indolyl, pyridazinyl, pyridinyl, pyrrolyl, pyranyl, pyrimidinyl, furanyl, triazolyl, tetrazolyl, benzofuranyl, benzoxazolyl, isoxazolyl, isothiazolyl, thiadiazolyl, thiophenyl, tetrahydrofurofuranyl, tetrahydropyranofuranyl, benzothiophenyl, carbazoyl, imidazolonyl, oxazolonyl, indolizinyl, triazinyl, quinoxalinyl, piperidinyl, piperazinyl, morpholinyl, thiamorpholinyl, pyrazinyl, thienyl, tetrahydroquinolinyl, tetrahydroisoquinolinyl, β-carbolinyl, dioxanyl, dithianyl, oxolanyl, dioxolanyl, tetrahydrothiophenyl, tetrahydropyranyl, tetrahydropyranyl; wherein G is optionally benzofused; wherein G is optionally further substituted on one or more ring members; preferably G is selected from thiazolyl, imidazolyl, oxazolyl, oxadiazolyl, pyrazolyl, pyridinyl, optionally substituted on one or more ring members.

A suitable group of compounds are those compounds of formula (I), wherein $R_2$ is hydrogen; $R_3$ is alkylaryl; and $R_4$ is $C_{1-4}$alkyl; in particular, $R_2$ is hydrogen; $R_3$ is methylaryl; and R is isobutyl.

A suitable group of compounds are those compounds of formula (I) as a salt, wherein the salt is selected from trifluoroacetate, fumarate, chloroacetate and methanesulfonate.

An interesting group of compounds are those compounds of formula (I) having a fold resistance, determined according to the methods herein described, in the range of 0.01 to 100 against HIV species having at least one mutation in the HIV protease as compared to the wild type sequence (e.g. M38432, K03455, gi 327742) at a position selected from 10, 71 and 84; in particular at least two mutations selected from 10, 71 and 84 are present in the HIV protease; in particular the compounds have a fold resistance in the range of 0.1 to 100, more in particular in the range 0.1 to 50, suitably in the range 0.2 to 35. An interesting group of compounds are compounds N° 1-8, 10, 12-13, 18-21, 23-24, 34-37, 39, 42-50, 53, 56, 58-59 as disclosed in the present invention.

A suitable group of compounds are compounds N° 1-3, 5-8, 18, 21, 23, 35, 46, 48-50, 53, 59 and 61 as disclosed in the instant invention.

The invention also concerns a pharmaceutical composition consisting of a solid dispersion comprising, (a) a compound as claimed in any of claim 1 tot 10, (b) one or more pharmaceutically acceptable water-soluble polymers. In particular, the compound is selected from compound N° 1-3,5-8, 18, 21, 23, 35, 46, 48-50, 53, 59 and 61.

Conveniently, a water soluble polymer includes hydroxypropylmethylcellulose, polyvinylpyrrolidone copolymer with vinyl acetate (PVP-VA).

Compounds having interesting pharmacokinetic properties are those of formula (I), containing at least one substituent independently selected from thiazole, imidazole and pyridine.

The compounds of formula (I) can generally be prepared using procedures analogous to those procedures described in WO 95/06030, WO 96/22287, WO 96/28418, WO 96/28463, WO 96/28464, WO 96/28465 and WO 97/18205.

Particular reaction procedures to make the present compounds are described below. In the preparations described below, the reaction products may be isolated from the medium and, if necessary, further purified according to methodologies generally known in the art such as, for example, extraction, crystallization, trituration and chromatography.

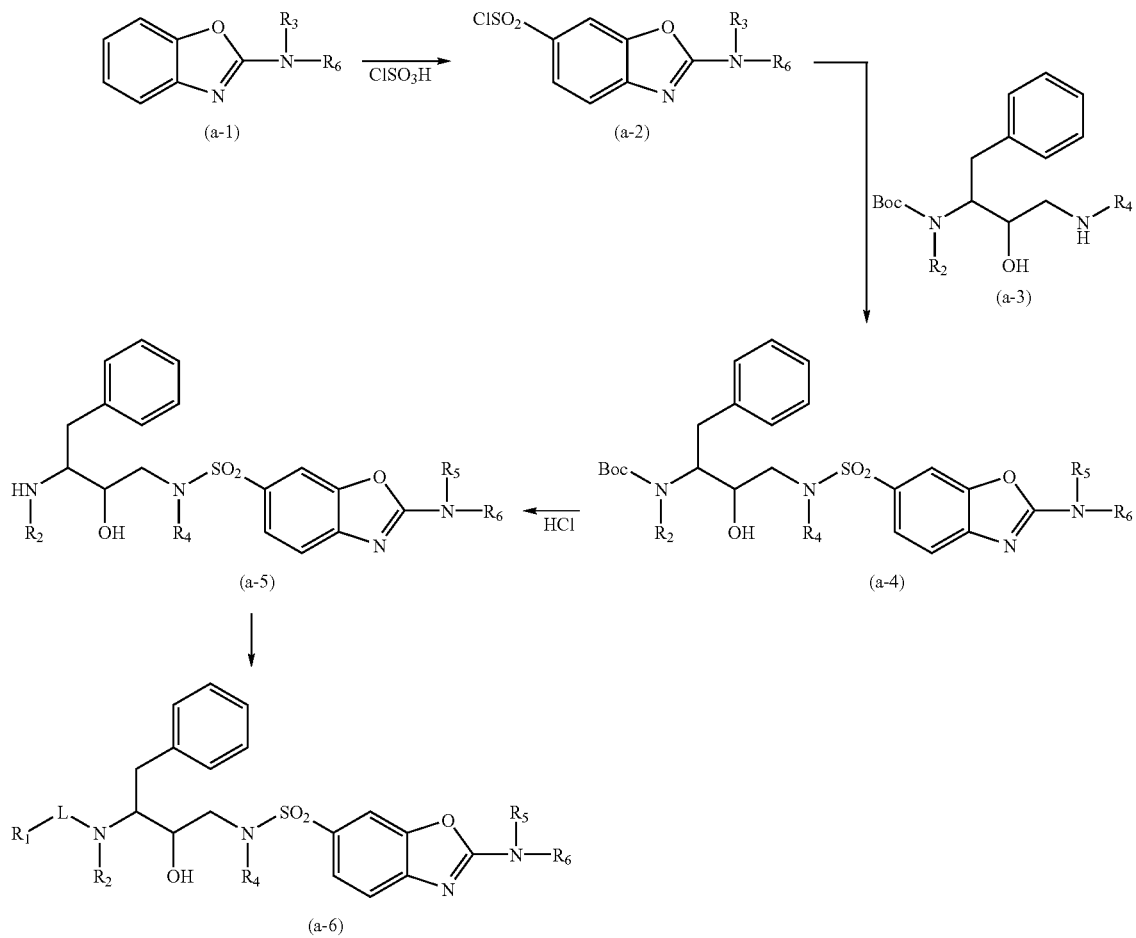

The 2-amino-6-chlorosulfonylbenzoxazole derivative (intermediate a-2) was prepared following the procedure described in EP-A-0,445,926. Intermediates a-4 were prepared by reacting an intermediate a-3, prepared according to the procedure I described in WO97/18205 and also depicted in scheme B, with an intermediate a-2 in a reaction-inert solvent such as dichloromethane, and in the presence of a base such as triethylamine and at low temperature, for example at 0° C. The Boc group in the intermediate a-3 is a protective tert-butyloxycarbonyl group. It may conveniently be replaced by another suitable protective group such as phtalimido or benzyloxycarbonyl.

Intermediates a-4 may be deprotected with an acid such as hydrochloric acid in isopropanol or with trifluoroacetic acid depending on the nature of the amino group in the 2 position of benzoxazole, in a suitable solvent such as a mixture of ethanol and dioxane, thus preparing an intermediate a-5. Said intermediate a-5 may be further reacted with an intermediate of formula $R_1$-L-(leaving group) in the presence of a base such as triethylamine (for alcohols to generate a carbamate) and optionally in the presence of 1-(3-dimethylaminopropyl)-3-ethylcarbodiimide hydrochloric acid (EDC) and I-hydroxybenzotriazole (HOBT)(for carboxylic acids to generate an amide) or an alcohol such as tert-butanol, and in a suitable solvent such as dichloromethane; thus forming intermediates a-6. Particularly, intermediates of formula $R_1$—C(=O)—OH are suitable to further react with an intermediate a-5.

A convenient way of preparing compounds of formula (I) wherein both $R_5$ and $R_6$ are hydrogen can be prepared analogously to the procedure described in scheme A, and whereby one of $R_5$ or $R_6$ is replaced by a suitable protective group such as, for example, an acetyl or an alkyloxycarbonyl group. In such a case, deprotection may occur simultaneously with the deprotection of the nitrogen atom on the left-hand side of the molecule.

A number of intermediates and starting materials used in the foregoing preparations are known compounds, while others may be prepared according to art-known methodologies of preparing said or similar compounds.

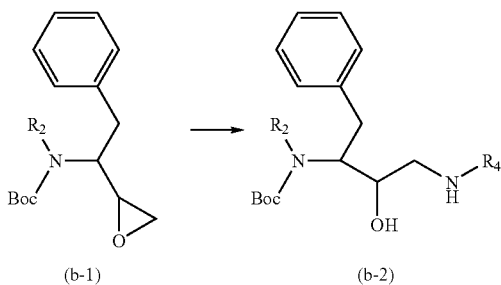

(b-1)   (b-2)

Intermediate b-2, corresponding to intermediate a-3 in scheme A, may be prepared by adding an amine of formula $H_2N$—$R_4$ to an intermediate b-I in a suitable solvent such as isopropanol.

In scheme B, enantiomerically pure compounds of formula b-2 are only obtained if b-I is enantiomerically pure. If b-1 is a mixture of stereoisomers, than b-2 will also consist of a mixture of stereoisomers.

One particular example of preparing intermediates of formula $R_1$-L-(leaving group) as used in scheme A is depicted in scheme C.

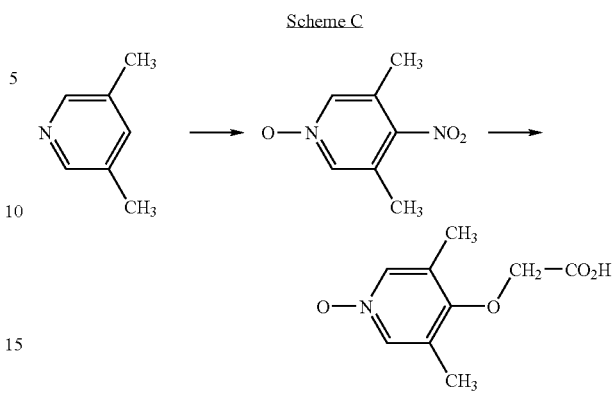

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide.

Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g., 2-butanone, halogenated hydrocarbons, e.g. dichloromethane, and mixtures of such solvents.

The present compounds can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds of formula (I) in addition to customary pharmaceutically innocuous excipients and auxiliaries. The pharmaceutical preparations normally contain 0.1 to 90% by weight of a compound of formula (1). The pharmaceutical preparations can be prepared in a manner known per se to one of skill in the art. For this purpose, at least one of a compound of formula (I), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Due to their favorable pharmacological properties, particularly their activity against multi-drug resistant HIV protease enzymes, the compounds of the present invention are useful in the treatment of individuals infected by HIV and for the prophylaxis of these individuals. In general, the compounds of the present invention may be useful in the treatment of warm-blooded animals infected with viruses whose existence is mediated by, or depends upon, the protease enzyme. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1. Consequently, the compounds of the present invention can be used in the manufacture of a medicament useful for treating conditions associated with HIV and other pathogenic retroviruses, in particular medicaments useful for treating patients infected with multi-drug resistant HIV virus.

In a preferred embodiment, the invention relates to the use of a compound of formula (I) or any subgroup thereof in the manufacture of a medicament for treating or combating infection or disease associated with multi-drug resistant retrovirus infection in a mammal, in particular HIV-I infection. Thus, the invention also relates to a method of treating a retroviral infection, or a disease associated with multi-drug resistant retrovirus infection comprising administering to a mammal in need thereof an effective amount of a compound of formula (I) or a subgroup thereof.

In another preferred embodiment, the present invention relates to the use of formula (I) or any subgroup thereof in the manufacture of a medicament for inhibiting a protease of a multi-drug resistant retrovirus in a mammal infected with said retrovirus, in particular HIV-I retrovirus.

In another preferred embodiment, the present invention relates to the use of formula (I) or any subgroup thereof in the manufacture of a medicament for inhibiting multi-drug resistant retroviral replication, in particular HIV-I replication.

The compounds of the present invention may also find use in inhibiting ex vivo samples containing HIV or expected to be exposed to HIV. Hence, the present compounds may be used to inhibit HIV present in a body fluid sample which contains or is suspected to contain or be exposed to HIV.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, 5-helix, D-peptide ADS-J I; co-receptor binding inhibitors, such as, for example, AMD 3100, AMD-3465, AMD7049, AMD3451 (Bicyclams), TAK 779; SHC-C (SCH351125), SHC-D, PRO-140RT inhibitors, such as, for example, foscarnet and prodrugs; nucleoside RTIs, such as, for example, AZT, 3TC, DDC, DDI, D4T, Abacavir, FTC, DAPD, dOTC, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, DPC 961, DPC963, DPC082, DPCO83, calanolide A, SJ-1366, TSAO, 4"-deaminated TSAO, MVI 50, MV026048; RNAse H inhibitors, such as, for example, SP1093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908, ritonavir, nelfinavir, saquinavir, indinavir, lopinavir, palinavir, BMS 186316, atazanavir, DPC 681, DPC 684, tipranavir, AG1776, mozenavir, GS3333, KNI-413, KNI-272, L754394, L756425, LG-71350, PD161374, PD173606, PD177298, PD178390, PD178392, PNU 140135, TMCI 14 maslinic acid, U-140690; glycosylation inhibitors, such as, for example, castanospermine, deoxynojirimycine.

The combination may in some cases provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, HE-2000 and naltrexone) with antibiotics (e.g., pentamidine isothiorate) cytokines (e.g. Th2), modulators of cytokines, chemokines or the receptors thereof (e.g. CCR5) or hormones (e.g. growth hormone) to ameliorate, combat, or eliminate HIV infection and its symptoms. Such combination therapy in different formulations, may be administered simultaneously, separately or sequentially. Alternatively, such combination may be administered as a single formulation, whereby the active ingredients are released from the formulation simultaneously or separately.

The compounds of the present invention may also be administered in combination with modulators of the metabolization following application of the drug to an individual.

These modulators include compounds that interfere with the metabolization at cytochromes, such as cytochrome P450. Some modulators inhibit cytochrome P450. It is known that several isoenzymes exist of cytochrome P450, one of which is cytochrome P450 3A4. Ritonavir is an example of a modulator of metabolization via cytochrome P450. Such combination therapy in different formulations, may be administered simultaneously, separately or sequentially. Alternatively, such combination may be administered as a single formulation, whereby the active ingredients are released from the formulation simultaneously or separately.

Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof.

Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds of formula (I) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated, β-CD, 2,6-dimethyl-β-CD, 2-hydroxyethyl-, β-CD, 2-hydroxyethyl-γ-CD, 2-hydroxypropyl-γ-CD and (2-carboxymethoxy)propyl-β-CD, and in particular 2-hydroxypropyl-, β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifuingal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavors.

Other convenient ways to enhance the solubility of the compounds of the present invention in pharmaceutical compositions are described in WO 94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (1), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC.

HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion.

Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm.

Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present compounds are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The route of administration may depend on the condition of the subject, co-medication and the like.

Another aspect of the present invention concerns a kit or container comprising a compound of formula (I) in an amount effective for use as a standard or reagent in a test or assay for determining the ability of a potential pharmaceutical to inhibit HIV protease, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K, de Bethune M P, Miller V et al. *Antimicrob Agents Chemother,* 1998; 42(2):269-276, incorporated by reference).

Interestingly, the compounds of the present invention may comprise chemically reactive moieties capable of forming covalent bonds to localized sites such that said compound have increased tissue retention and half-lives. The term "chemically reactive group" as used herein refers to chemical groups capable of forming a covalent bond.

Reactive groups will generally be stable in an aqueous environment and will usually be carboxy, phosphoryl, or convenient acyl group, either as an ester or a mixed anhydride, or an imidate, or a maleimidate thereby capable of forming a covalent bond with functionalities such as an amino group, a hydroxy or a thiol at the target site on for example blood components such as albumine. The compounds of the present invention may be linked to maleimide or derivatives thereof to form conjugates.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight, co-medication, and individual responsiveness of the human or animal to be treated and on whether the therapy is acute or prophylactic. Customarily, the daily dose of a compound of formula (I) in the case of administration to a patient approximately 75 kg in weight is 1 mg to 3 g, suitably 1 mg to 1 g, preferably 3 mg to 0.5 g, more preferably 5 mg to 300 mg. The dose can be administered in the form of an individual dose, or divided into several, e.g. two, three, or four, individual doses.

EXPERIMENTAL PART

Example 1

Preparation of Compound 3

To a mixture of 300 mg 5-hydroxymethylthiazole and 789 mg triethylamine in dichloromethane was added 735 mg of DSC(N,N'-disuccinimidyl carbonate). After 6 hours stirring at room temperature the organic phase was washed with saturated bicarbonate solution. After drying over $MgSO_4$, the solvent was filtered, whereafter 525 mg triethylamine and 1.1 g of intermediate a-5 [$R_2$, $R_5$ and $R_6$ are hydrogen and $R_4$=—$CH_2$—$CH(CH_3)_2$] were added. After overnight stirring the solvent was evaporated under vacuum. Purification by column chromatography yielded 800 mg of compound 3.

Example 2

Preparation of Compound 5

A mixture of 1 g of intermediate a-5 [$R_2$, $R_5$ and $R_6$ are hydrogen and $R_4$=—$CH_2$—$CH(CH_3)_2$], 78 mg of HOBT (hydroxybenzotriazol), 488 mg of EDC and 416 mg of 2-(2,6-dimethylphenoxy)acetic acid in 120 ml of dichloromethane, was stirred overnight at room temperature. The reaction mixture was then washed with 5% HCl, sat. $NaHCO_3$ solution and brine. The organic layer was separated, dried and the solvent evaporated. The residue was purified by column chromatography. 1.3 g of compound 5 was obtained with a yield of 98%.

Example 3

Preparation of Compound 7

To a mixture of 259 mg intermediate a-5 [$R_2$, $R_5$ and $R_6$ are hydrogen and $R_4$=—$CH_2$—$CH(CH_3)$;] and 60 mg triethylamine in dichloromethane was added 163 mg 1-[[[[(3R,3aS,6aR)-hexahydrofuro[2,3-b]furan-3-yl]oxy]carbonyl]oxy]-2,5-pyrrolidione-dione (described in WO9967417). This mixture was stirred a room temperature for 12 hours. After evaporation of dichloromethane under reduced pressure, the crude product was purified on silica, yielding 340 mg of compound 7 (96%).

Example 4

Preparation of Compound 8 and Salts a) To a mixture of 289 mg intermediate a-5 [$R_2$ and $R_5$ are hydrogen, $R_6$ is $CH_3$ and $R_4$=—$CH_2$—$CH(CH_3)_2$] and 70 mg triethylamine in dichloromethane was added 176 mg 1-[[[[(3R,3aS,6aR)-hexahydrofuro[2,3-b]furan-3-yl]oxy]carbonyl]oxy]-2,5-pyrrolidine-dione (described in WO9967417). This mixture was stirred at room temperature for 12 hours. After evaporation of dichloromethane under reduced pressure, the crude product was purified on silica, yielding 343 mg of compound 8 (94%).

b) 1 g of compound 8 was dissolved in tetrahydrofuran with heating. 160 mg methane-sulfonic acid in tetrahydrofuran was added. After 5 minutes precipitation was observed. After 30 minutes stirring and cooling to room temperature the precipitate was filtered. Drying under reduced pressure yielded 889 mg of compound 48 (77%).

The hydrochloride (compound 49) and fumarate salts (compound 50) were prepared in an analogous manner.

Example 5

Preparation of Compound 45 a) A mixture of 1.7 g of 4-nitropyridine-3,5-lutidine N-oxyde (prepared as described WO 99/10326 or EP 0103 553 A1), 2.1 g of ethyl glycolate and 1.4 g of potassium carbonate was warmed at 60° during 4 hours (h). This crude material was directly purified by column chromatography yielding 1.8 g (80%) of ethyl 3,5-dimethyl-pyridin-N-oxyde-4-oxy-acetic. This compound was stirred during one hour in 20 ml ethanol/water 1/1 and 1.4 g of potassium carbonate. A solid was formed and filtered off yielding 1.5 g (95%) of 2,4-dimethyl-pyridin-N-oxyde-3-oxy-acetic (see scheme C).

b) A mixture of 0.43 g of intermediate a-5 [$R_2$, $R_5$ and $R_6$ are hydrogen and $R_4$=—$CH_2$—$CH(CH_3)_2$], 50 mg of HOBT (hydroxybenzotriazol), 197 mg of EDC and 197 mg of 3,5-dimethyl-pyridin-N-oxyde-4-oxy-acetic in 10 ml of N,N-dimethylformamide, was stirred overnight at room temperature. The solvent was evaporated, then washed with 5% HCl, sat. $NaHCO_3$ solution and brine. The organic layer was separated, dried and evaporated. The residue was purified by column chromatography, yielding 300 mg of compound 45 (50%).

Example 6

Preparation of Compound 46

A mixture of 250 mg of compound 45, 250 mg of palladium hydroxide and 1 g of ammonium formate in 10 ml methanol was stirred overnight at refluxed. This crude product was filtered on decalite, the filtrate evaporated and purified on column chromatography yielding 72 mg (28%) of compound 46.

Example 7

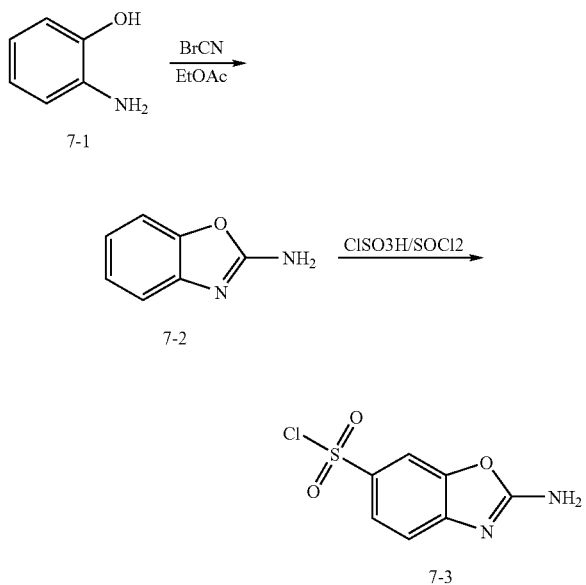

A mixture of 2.5 g 2-aminophenol (7-1) and 20 ml ethyl acetate was heated to 45° C. 3 g of cyanogen bromide was added to the mixture. The mixture was stirred at 45-50° C. for 12 hours. After cooling to room temperature, 1.5 g of sodium hydroxide in 15 ml of water was added. The organic layer was separated and washed with brine until neutral pH. Toluene (5 ml) was added and the solvent was removed to yield 2.71 g (88%) 2-aminobenzoxazol (7-2).

7.5 ml of chlorosulfonic acid was stirred at room temperature under an inert atmosphere (nitrogen). 5 g of 2-aminobenzoxazol (7-2) was added in small portions. The temperature was kept between 30-60° C. during the addition of 7-2. The mixture was heated to 80° C. for 2 hours. 5.3 g of thionyl chloride was added drop wise, keeping the temperature at 65° C. The mixture was stirred during 2 hours. After cooling to 0° C. 0.10 ml of ethyl acetate and 10 ml of a solution of sodium carbonate (1N) were added. The organic layer was separated from the water layer and this latter was extracted with ethyl acetate. The combined organic layers were dried over calcium chloride, yielding 7.8 g (90%) of 2-amino-6-chlorosulfonyl-benzoxazole (7-3).

Example 8

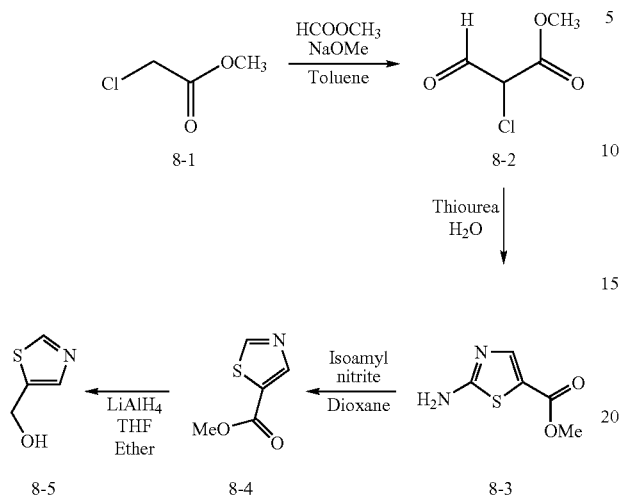

A mixture of 1 g of sodium methoxide and 10 ml of toluene was stirred at 0° C. under nitrogen atmosphere. A mixture of 1.9 g of methyl chloracetate (8-1) and 1.1 g of methylformate was added drop wise keeping the temperature between 5-10° C. The mixture was stirred for 2 hours at 0° C. After washing with water, the organic layer was dried and evaporated under reduced pressure yielding 2-chloro-3-oxo-propionic acid methyl ester (8-2).

A mixture of 2.4 g of 2-chloro-3-oxo-propionic acid methyl ester (8-2), water 20 ml and 1.75 g of thiourea was refluxed for 2 hours. The mixture was cooled to room temperature and 0.25 g of norit was added and filtered. A solution of 2.5N sodium hydroxide was added to the filtrate until neutral pH. The filtration yielded 1.23 g (44%) of 2-aminothiazole-5-carboxylic acid methyl ester (8-3).

The mixture of 2.15 g of isoamyl nitrite and 10 ml of dioxane was stirred at 80° C. under a nitrogen atmosphere. A solution of 1.23 g of 2-aminothiazole-5-carboxylic acid methyl ester (8-3) in 20 ml of dioxane was added drop wise. The mixture was refluxed for 2 hours. After cooling to room temperature 30 ml of ethyl acetate was added. The mixture was washed with brine and dried and the solvent evaporated under reduced pressure. The crude product is purified on silica, yielding 0.54 g (48%) of thiazol 5-carboxylic acid methyl ester (84).

A mixture of 0.54 g of thiazol 5-carboxylic acid methyl ester (8-4) and 10 ml tetrahydro-furane (THF) was stirred at 0° C. under a nitrogen atmosphere. The mixture of 0.16 g of lithium aluminium hydride and 5 ml of ether was added drop wise. After 1 hour at 0° C. water and 20% sodium hydroxide were added, and stirred during 30 minutes (min). The mixture was filtered over decalite and the solvent was removed by azeotropique distillation with toluene yielding 0.3 g (69%) of thiazol-5-yl-methanol (8-5).

Example 9

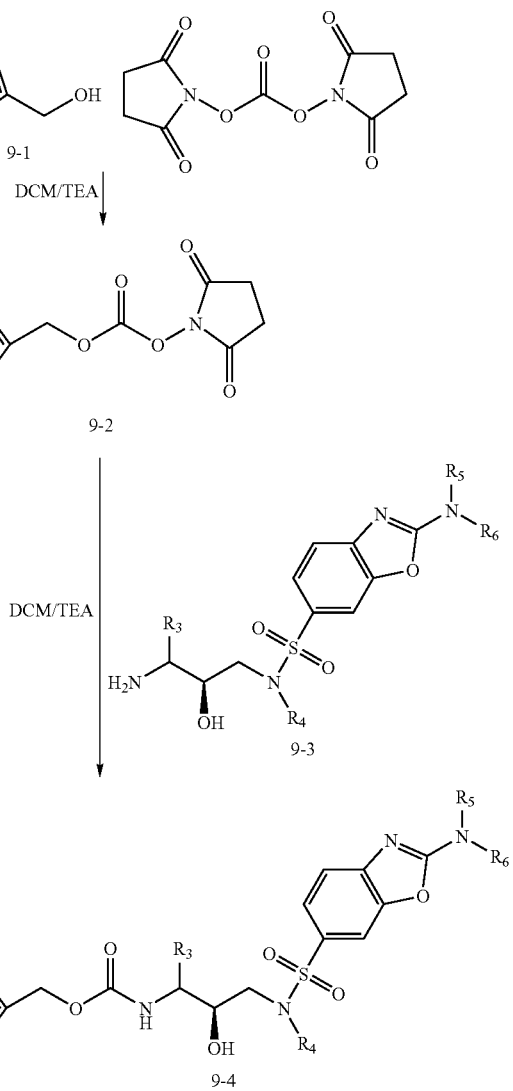

A mixture of 1.15 g of thiazol-5-yl-methanol (9-1) and 1.2 g triethylamine (TEA) in 25 ml of dichloromethane (DCM) was stirred at room temperature under an atmosphere of nitrogen. 2.56 g of N,N'-disuccinimidyl carbonate was then added and the resulting mixture was stirred for 10-15 minutes. The solution was stirred for an additional 2 hours. The resulting intermediate (9-2) was used directly in the subsequent reaction with the amine (9-3). Instead of amines also salts thereof can be used.

Triethylamine 2 g and the amine 5 g (9-3) were added to dichloromethane 40 ml and the resulting mixture was stirred at room temperature. Subsequently, a portion of the solution comprising 9-2 was added drop wise. The reaction mixture was stirred at room temperature for 2 hours. The reaction mixture was washed with water and then dried to yield compound (9-4).

The following compounds were prepared analogous to any one of the above examples:

TABLE 1

Compounds (Co. N°) of the present invention prepared according to the methods described above. If no stereochemistry is indicated, the compound is present as a racemic mixture.

Compound 60

| Co. N° | R$_a$ | R$_b$ | Scheme | Co. N° | R$_a$ | R$_b$ | Scheme |
|---|---|---|---|---|---|---|---|
| 1 | tetrahydrofuran-3-yl-O-methyl | —NH$_2$ | A | 33 ① | pyrido-dioxine-CH$_2$-O-methyl | —NH$_2$ | A |
| 2 | hexahydrofuro-furan-methoxy | —NH$_2$ | A | 34 | 2,6-dimethyl-3,4-diamino-phenyl-OCH$_2$ | —NH$_2$ | A |
| 3 | thiazol-5-yl-CH$_2$-O-methyl | —NH$_2$ | Ex. 9 | 35 | dimethyl-benzimidazol-O-ethyl | —NH$_2$ | A |
| 4 | pyridin-3-yl-CH$_2$-O-methyl | —NH$_2$ | A | 36 | 2,6-dimethylphenoxy-CH(CH$_3$)-CH$_2$OH | —NH$_2$ | A |
| 5 | 2,6-dimethylphenoxy-CH$_2$- | —NH$_2$ | A | 37 | dimethyl-imidazo-thiazolyl | —NH$_2$ | A |
| 6 | 2,3-dimethyl-aniline | —NH$_2$ | A | 38 | 4-bromo-2,3-dimethylphenyl | —NHCH$_3$ | A |
| 7 | hexahydrofuro-furan-O-methyl | —NH$_2$ | A | 39 | imidazol-5-yl-CH$_2$-O-methyl | —NH$_2$ | A |

TABLE 1-continued

Compounds (Co. N°) of the present invention prepared according to the methods described above. If no stereochemistry is indicated, the compound is present as a racemic mixture.

Compound 60

| Co. N° | R$_a$ | R$_b$ | Scheme | Co. N° | R$_a$ | R$_b$ | Scheme |
|---|---|---|---|---|---|---|---|
| 8 | [hexahydrofuro[2,3-b]furan-3-yloxy] | —NHCH$_3$ | A | 40 | [(2-hydroxymethyl)thiazol-4-yl]methoxy | —NH$_2$ | Ex. 9 |
| 9 ① | [(3R)-3-methoxytetrahydrofuran] | —NHCH$_3$ | A | 41 | [4-ethoxy-3,5-dimethylbenzyl]amine | —NH$_2$ | A |
| 10 ① | [thiazol-5-yl-methoxy] | —NHCH$_3$ | Ex 9 | 42 | [3,5-dimethyl-4-(2-methoxyethoxy)pyridine] | —NH$_2$ | A |
| 11 ① | [2-methyl-3-hydroxyphenyl] | —NHCH$_3$ | A | 43 | [hexahydrofuro-morpholine methoxy A/B (28%A/72%B)] | —NHCH$_3$ | A |
| 12 ① | [3-amino-2-methylphenyl] | —NHCH$_3$ | A | 44 | [hexahydrofuro-morpholine methoxy A/B (70%A/30%B)] | —NHCH$_3$ | A |
| 13 ① | [2-ethoxy-3,5-dimethylphenyl] | —NHCH$_3$ | A | 45 | [4-ethoxy-3,5-dimethylpyridine N-oxide] | —NH$_2$ | A |
| 14 | [3,5-dichloro-4-ethoxypyridine] | —NHCH$_3$ | A | 46 | [4-ethoxy-3,5-dimethylpyridine] | —NH$_2$ | A |

TABLE 1-continued

*Compounds (Co. N°) of the present invention prepared according to the methods described above. If no stereochemistry is indicated, the compound is present as a racemic mixture.*

| Co. N° | $R_a$ | $R_b$ | Scheme | Co. N° | $R_a$ | $R_b$ | Scheme |
|---|---|---|---|---|---|---|---|
| 15 | (structure A / structure B) (50%A/50%B) | —NHCH₃ | A | 47 | (oxazolidinone-pyrrolidine methoxy structure) | —NH₂ | A |
| 16 | (4,5-dimethylisoxazole) | —NHCH₃ | A | 48 ② | (bicyclic furan-methoxy structure) | —NHCH₃ | A |
| 17 | (2,6-dimethyl-4-nitrophenyl ethoxy) | —NHCH₃ | A | 49 ③ | (bicyclic furan-methoxy structure) | —NHCH₃ | A |
| 18 | (2,6-dimethyl-4-amino phenyl ethoxy) | —NHCH₃ | A | 50 ④ | (bicyclic furan-methoxy structure) | —NHCH₃ | A |
| 19 | (morpholino-furan methoxy structure) | —NH₂ | A | 51 | (2-chloro-thiazole-methoxymethyl) | —NH₂ | Ex. 9 |
| 20 ① | (morpholino-furan methoxy structure) | —NH₂ | A | 53 | (oxazole-methoxymethyl) | —NH₂ | A |
| 21 | (4-bromo-2-methylphenyl) | —NH₂ | A | 54 | (3,5-dihydroxycyclohexyl methyl) | —NH₂ | A |

Compound 60 (structures shown at top of table)

TABLE 1-continued

Compounds (Co. N°) of the present invention prepared according to the methods described above. If no stereochemistry is indicated, the compound is present as a racemic mixture.

Compound 60

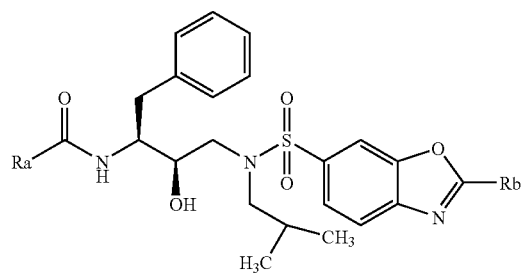 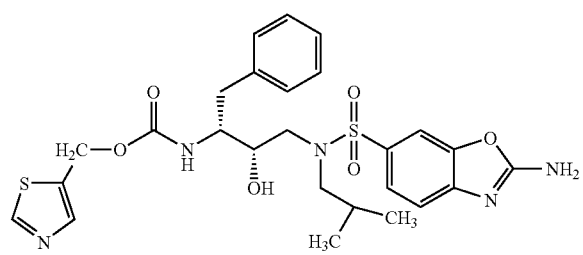

| Co. N° | $R_a$ | $R_b$ | Scheme | Co. N° | $R_a$ | $R_b$ | Scheme |
|---|---|---|---|---|---|---|---|
| 22 | 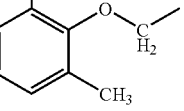 | —NH$_2$ | A | 55 | 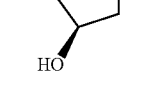 | —NH$_2$ | A |
| 23 ① | 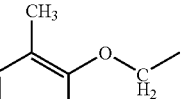 | —NH$_2$ | A | 56 | 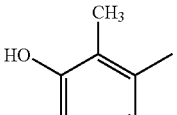 | —NH$_2$ | A |
| 24 | 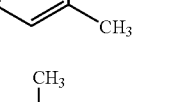 | —NH$_2$ | A | 58 | 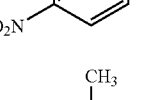 | —NH$_2$ | A |
| 26 | 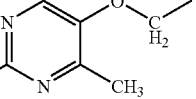 | —NH$_2$ | A | 59 | 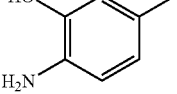 | —NH$_2$ | A |
| 27 | 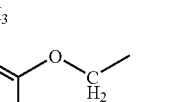 | —NH$_2$ | Ex 9 | 60 | see top | see top | Ex. 9 |
| 32 ① | 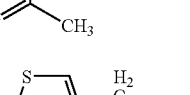 | —NH$_2$ | A | 61 | 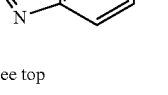 | —NH$_2$ | A |
| 52 | 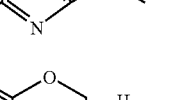 | —N(CH$_3$)$_2$ | Ex. 9 | 62 | 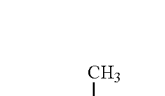 | —N(CH$_3$)$_2$ | |

① Trifluoroacetate salt
② methanosulfonate salt
③ Chlorohydrate salt
④ fumarate salt

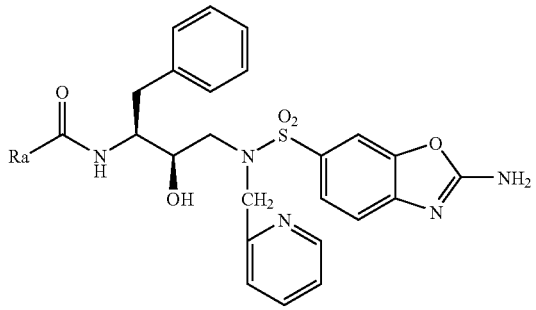

| Co. N° | Ra | Synthesis Scheme | Co. N° | Ra | Synthesis Scheme |
|---|---|---|---|---|---|
| 25 | (structure: oxabicyclic with OMe) | A | 30 ① | (2,6-dimethylphenyl-OCH2CH3) | A |
| 28 ① | (pyridin-3-yl-CH2-O-) | A | 31 ① | (2,3-dimethyl-6-hydroxyphenyl) | A |
| 29 ① | (thiazol-5-yl-CH2-O-) | Ex. 9 | 57 ① | ((R)-tetrahydrofuran-3-yl-O-) | A |
| 63 | (pyridin-3-yl-CH2-O-) | A | 64 | (2,6-dimethylphenyl-OCH2CH3) | A |
| 65 | (thiazol-5-yl-CH2-O-) | Ex. 9 | 66 | ((R)-tetrahydrofuran-3-yl-O-) | A |
| 67 | (2,3-dimethyl-6-hydroxyphenyl) | A | | | |

① Trifluoroacetate salt

Antiviral Analyses:

The compounds of the present invention were examined for anti-viral activity in a cellular assay. The assay demonstrated that these compounds exhibited potent anti-HIV activity against a wild type laboratory HIV strain (HIV-1 strain LAI). The cellular assay was performed according to the following procedure.

Cellular Assay Experimental Method:

HIV- or mock-infected MT4 cells were incubated for five days in the presence of various concentrations of the inhibitor. At the end of the incubation period, all HIV-infected cells have been killed by the replicating virus in the control cultures in the absence of any inhibitor. Cell viability is measured by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution is monitored at 540 nm. The values correlate directly to the number of living cells remaining in the culture at the completion of the five day incubation. The inhibitory activity of the compound was monitored on the virus-infected cells and was expressed as $EC_{50}$ and $EC_{90}$. These values represent the amount of the compound required to protect 50% and 90%, respectively, of the cells from the cytopathogenic effect of the virus. The toxicity of the compound was measured on the mock-infected cells and was expressed as $CC_{50}$, which represents the concentration of compound required to inhibit the growth of the cells by 50%. The selectivity index (SI) (ratio $CC_{50}/EC_{50}$) is an indication of the selectivity of the anti-HIV activity of the inhibitor. Whetever results are reported as e.g. $pEC_{50}$ or $pCC_{50}$ values, the result is expressed as the negative logarithm of the result expressed as $EC_{50}$ or $CC_{50}$ respectively.

The SI for the tested compounds ranges between more than 10 up to more than 10000.

Antiviral Spectrum:

Because of the increasing emergence of drug resistant HIV strains, the present compounds were tested for their potency against clinically isolated HIV strains harboring several mutations (Table 2 and 3). These mutations are associated with resistance to protease inhibitors and result in viruses that show various degrees of phenotypic cross-resistance to the currently commercially available drugs such as for instance saquinavir, ritonavir, nelfinavir, indinavir and amprenavir.

TABLE 2

List of mutations present in the protease gene of the HIV strains (A to F) used.

A  V003I, L010I, V032T, L033M, E035D, S037Y, S037D, M046I, R057R/K, Q058E, L063P, K070T, A071V, I072V, I084V, L089V
B  V003I, L010I, K020R, E035D, M036I, S037N, Q058E, I062V, L063P, A071V, I072M, G073S, V077I, I084V, I085V, L090M
C  V003I, L010I, I015V, L019I, K020M, S037N, R041K, I054V, Q058E, L063P, A071V, I084V, L090M, I093L
D  V003I, L010L/I, I013V, L033I, E035D, M036I, M046L, K055R, R057K, L063P, I066F, A071V, I084V, N088D, L090M
E  V003I, L010I, V011I, A022V, L024I, E035D, M036I, S037T, R041K, I054V, I062V, L063P, A071V, I084V
F  L010F, M046I, M071V, I084V

Results:

As a measure of the broad spectrum activity of the present compounds, the fold resistance (FR), defined as $FR=EC_{50}$ (mutant strain)/EC50(HIV-I strain LAI), was determined. Table 3 shows the results of the antiviral testing in terms of fold resistance. As can be seen in this table, the present compounds are effective in inhibiting a broad range of mutant strains: Column A: FR value towards mutant A, Column B: FR towards mutant B, Column C: FR towards mutant C, Column D: FR towards mutant D, Column E: FR towards mutant E, Column F: FR towards mutant F. The toxicity (Tox) is expressed as the $pCC_{50}$ value as determined with mock transfected cells. Column WT displays the pEC50 value against wild type HIV-LAI strain.

TABLE 3

Results of the toxicity testing and the resistance testing against strain A to F (expressed as FR).

| Comp. N° | A | B | C | D | E | F | Tox | WT |
|---|---|---|---|---|---|---|---|---|
| 1 | 17 | 3.1 | 2.2 | 1.9 | 1.2 | 21 | 4 | 8.12 |
| 2 | 0.27 | 0.19 | 0.19 | 0.17 | 0.17 | 1.3 | 4 | 7.48 |
| 3 | 3.1 | 1.3 | 1.4 | 2.5 | 1.5 | 14 | 4 | 8.18 |
| 4 | 14 | 1.7 | 2.2 | 9.5 | 2.5 | 50 | 4 | 7.81 |
| 5 | 2.3 | 0.78 | 1.6 | 1.7 | 1.62 | 8.5 | 4.26 | 7.8 |
| 6 | 3.5 | 0.62 | 0.64 | 0.74 | 0.68 | 4.3 | 4 | 7.27 |
| 7 | 0.27 | 0.34 | 0.22 | 0.18 | 0.20 | 0.51 | 4 | 7.7 |
| 8 | 2.1 | 1.2 | 0.83 | 0.71 | 0.63 | 1.0 | 4 | 8.57 |
| 9 | 79 | 4.7 | 4.7 | 5.4 | 4.5 | 115 | 4 | 8.11 |
| 10 | 37 | 13 | 7.4 | 16.2 | 8.3 | 36 | 4 | 7.98 |
| 11 | 87 | 3.5 | 3.7 | 3.5 | 2.63 | 224 | 4.09 | 8.03 |
| 12 | 37 | 5.1 | 7.2 | 6.8 | 4.4 | 40 | 4 | 7.69 |
| 13 | 3.7 | 0.85 | 3.7 | 3.5 | 2.6 | 7.1 | 4.03 | 7.33 |
| 18 | 10 | 3.0 | 3.8 | 4.7 | 3.3 | 55 | 4.11 | 8.46 |
| 19 | 0.2 | 0.25 | 0.25 | 0.17 | 0.21 | 0.63 | 4.34 | 6.17 |
| 20 | 0.23 | 0.30 | 0.30 | 0.20 | 0.25 | 0.63 | 4.34 | 6.25 |
| 21 | 4.7 | 0.68 | 0.74 | 2.3 | 0.60 | 13.5 | 4.29 | 8.10 |
| 23 | 7.4 | 2.0 | 9.3 | 8.9 | 9.3 | 35 | 4 | 7.06 |
| 24 | 12.3 | 0.83 | 0.81 | 1.0 | 0.78 | 62 | 4.0 | 7.41 |
| 26 | 72 | 4.1 | 8.1 | 9.1 | 3.0 | 170 | 4 | 7.23 |
| 34 | 6.8 | 1.7 | 2.2 | 2.3 | 2.2 | 8.9 | 4.16 | 7.02 |
| 35 | 58 | 13.2 | 7.2 | 8.9 | 8.1 | ND | 3.74 | 8.88 |
| 36 | ND | ND | 2.1 | ND | 2.2 | ND | 4.25 | 5.79 |
| 37 | 10 | 3.2 | 8.3 | 11 | 4.3 | 14 | 4 | 6.67 |
| 39 | ND | ND | 2.6 | 3.5 | 4.6 | ND | 4.5 | 5.87 |
| 42 | ND | 1.7 | 1.6 | 5.5 | 4.8 | ND | 4.15 | 6.28 |
| 43 | 3.3 | 1.6 | 0.8 | 0.62 | 0.59 | 14 | 4 | 7.32 |
| 44 | 1.6 | 1.3 | 0.93 | 0.56 | 0.56 | 4.9 | 4 | 7.36 |
| 45 | 7.9 | 1.4 | 1.3 | 1.5 | 1.5 | 17 | 4 | 6.23 |
| 46 | 3.2 | 0.83 | 2.2 | 4.0 | 19 | 13 | 4 | 8.07 |
| 47 | 0.5 | 0.48 | 0.36 | 0.53 | 0.23 | 3.4 | 4 | 6.65 |
| 48 | 3.7 | 0.72 | 0.45 | 0.87 | 0.93 | 19 | 4 | 8.8 |
| 49 | 3.2 | 0.74 | 0.63 | 0.69 | 0.71 | 17 | 4 | 8.78 |
| 50 | 3.5 | 0.72 | 0.54 | 0.72 | 0.76 | 17 | 4 | 8.77 |
| 53 | 4.6 | 1.4 | 1.2 | 3.1 | 1.2 | 13 | 4 | 8.14 |
| 56 | 2.6 | 0.76 | 1.1 | 3.8 | 1.4 | 6.6 | 4.3 | 7.49 |
| 58 | 0.60 | 0.45 | 0.46 | 0.52 | 0.44 | 0.98 | <4.49 | 6.45 |
| 59 | 19 | 0.87 | 1.32 | 4.4 | 0.98 | 28 | <4.49 | 8.11 |
| 61 | 83 | 5.9 | 2.1 | 3.2 | 0.78 | 214 | 4.3 | 7.97 |

ND indicates not determined

Caco-2 Permeability Assay for Intestinal Absorption

The permeability of different compounds is evaluated according to a Caco-2 test protocol as described by Augustijns et al. (Augustijns et al. (1998). *Int. J. of Pharm*, 166, 45-54) whereby, Caco-2 cells at cell passage number between 32 and 45 are grown in 24-well transwell cell culture plates for 21 to 25 days. The integrity of the cell monolayer is checked by measuring the transepithelial electrical resistance (TEER). The test is performed at pH 7.4 and at 100 μM donor compound concentration. Successive samples are taken at the receptor side to calculate the cumulative amounts and the apparent permeability.

Aqueous Solubility at Different pH Levels

The equilibrium solubility in simulated gastrointestinal solutions under thermodynamic conditions is a good measure for the solubility profile of the compound in the stomach and the different parts of the intestine. Simulated gastric fluid (SGF) (without pepsin) is set at pH of 1.5. Simulated intestinal fluids (SIF) (without bile salts) are set at pH 5, pH 6.5, pH 7 and pH 7.5. The experimental protocol uses 96-well flat-bottom microplates in which 1 mg of compound is added per well (stock solution in methanol) and evaporated to dryness. The compounds are resolubilized in SGF and SIF and incubated overnight on a horizontal shaking device at 37° C. After filtration, the compound concentrations are determined by UV-spectrophotometry.

Oral Availability in the Rat and the Dog

The oral availability of a series selected compounds is evaluated in a standard set of kinetic experiments, primarily in male and female rats and secondarily in male and female dogs. The compounds are formulated as a 20 mg/ml solution or suspension in DMSO, PEG400 or cyclodextin 40% (CD40%) in water. For most experiments in the rat, three dosing groups were formed: 1/single intraperitoneal dose at 20 mg/kg using the DMSO formulation; 2/single oral dose at 20 mg/kg using the PEG400 formulation and 3/single oral dose at 20 mg/kg using the cyclodextrin formulation. In the dog, only the oral route of administration is used. Blood is sampled at regular time intervals after dosing and serum drug concentrations are determined using a LC-MS bioanalytical method.

Boosting the Systemic Bioavailability

With the described type of compounds (protease-inhibitors), it is known that inhibition of the metabolic degradation processes can markedly increase the systemic availability by reducing the first-pass metabolism in the liver and the metabolic clearance from the plasma. This 'boosting' principle can be applied in a clinical setting to the pharmacological action of the drug. This principle can be also explored both in the rat or the dog by simultaneous administration of a compound that inhibits the Cyt-p450 metabolic enzymes. Known blockers are for example ritonavir and ketoconazole. Dosing a single oral dose of ritonvir (RTV) at 5 mg/kg in the rat and the dog may result in a marked increase of the systemic availability (reflected by the increased AUC) of the compound of the present invention added.

Protein Binding Analyses:

Human serum proteins like albumin (HSA) or α-1 acid glycoprotein (AAG) are known to bind many drugs, which may affect the effectiveness of those compounds. The anti-HIV activity of the compounds was measured in the presence of human serum, thus evaluating the effect of the binding of the protease inhibitors to those proteins.

MT4 cells are infected with HIV-1 LAI at a multiplicity of infection (MOI) of 0.001-0.01 $CCID_{50}$ (50% cell culture infective dose per cell, $CCID_{50}$). After 1 hour incubation, cells are washed and plated into a 96 well plate containing serial dilutions of the compound in the presence of 10% FCS (foetal calf serum), 10% FCS+1 mg/ml AAG ($α_1$-acid glycoprotein), 10% FCS+45 mg/ml HSA (human serum albumin) or 50% human serum (HS). After 5 or 6 days incubation, the $EC_{50}$ (50% effective concentration in cell-based assays) is calculated by determining the cell viability or by quantifying the level of HIV replication. Cell viability is measured using the assay described above. Into a 96 well plate containing serial dilutions of the compound in the presence of 10% FCS or 10% FCS+1 mg/ml AAG, HIV (wild type or resistant strain) and MT4 cells are added to a final concentration of 200-250 $CCID_{50}$/well and 30,000 cells/well, respectively. After 5 days of incubation (37° C., 5% $CO_2$), the viability of the cells is determined by the tetrazolium colorimetric MTT (3-[4,5-Dimetbylthiazol-2-yl]-2,5-di-phenyltetrazolium bromide) method (Pauwels et al. J. Virol. Methods 1988, 20, 309321).

Formulation of Compound 3

Compound 3 was dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropylmethylcellulose (HPMC), typically 5 mPa·s, were dissolved in organic solvents such as ethanol, methanol methylene chloride. Suitably the polymer was dissolved in ethanol. The polymer and compound solutions were mixed and subsequently spray dried. The ratio of compound/polymer was selected from 1/1 to 1/6.

Intermediate ranges are 1/1.5 and 1/3. A suitable ratio was 1/6. The spraydried powder, a solid dispersion, was subsequently filled in capsules for administration. The drug load in one capsule ranges between 50 and 100 mg depending on the capule size used.

Film-coated Tablets

Preparation of Tablet Core

A mixture of 100 g of active ingredient, 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.

Coating

To a solution of 10 g methylcellulose in 75 ml of denaturated ethanol there was added a solution of 5 g of ethylcellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was bomogenated. The tablet cores were coated with the thus obtained mixture in a coating apparatus.

The invention claimed is:

1. A compound having the formula

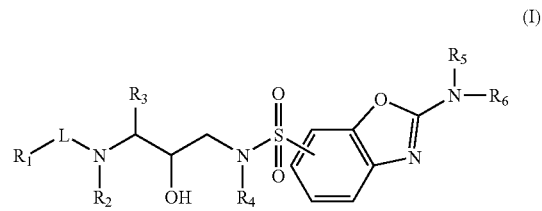

(I)

an N-oxide, salt, stereoisomeric form, racemic mixture, prodrug, or ester thereof, wherein $R_1$ is hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^1$, or Het$^1C_{1-6}$alkyl;

$R_2$ is hydrogen or $C_{1-6}$alkyl;

L is —C(=O)—, —O—C(=O)—, $NR_8$—C(=O)—, or —O—$C_{1-6}$alkanediyl-C(=O)—;

$R_3$ is $C_{1-6}$alkyl, aryl, $C_{3-7}$cycloalkyl, $C_{3-7}$cycloalkyl$C_{1-4}$alkyl, or aryl$C_{1-4}$alkyl;

$R_4$ is $C_{1-6}$alkyl optionally substituted with pyridinyl;

$R_5$ is hydrogen or $C_{1-6}$alkyl;

$R_6$ is hydrogen or $C_{1-6}$alkyl;

$R_8$ is hydrogen or $C_{1-6}$alkyl; and wherein

Het$^1$ is a saturated, or partially saturated, monocyclic, bicyclic or tricyclic heterocycle having 3 to 14 ring members, which contains 1 or more heteroatom ring members each independently selected from nitrogen, oxygen or sulfur, and which is optionally substituted on 1 or more carbon atoms by methyl, bromo, hydroxy, nitro, or cyano.

2. A compound according to claim 1, wherein $R_1$-L is Het$^1$-O—C(=O)—, or Het$^1C_{1-6}$alkyl-O—C(=O)—.

3. A compound according to claim 1, wherein $R_1$-L is Het$^1$ $C_{1-6}$alkanediyl-O—C(=O)—, aryl-O—$C_{1-6}$alkanediyl-C(=O)— or aryl-C(=O)—.

4. A compound according to claim 1, wherein $R_1$ is Het$^1$ or Het$^1C_{1-6}$alkyl; wherein said Het$^1$ comprises at least one heteroatom independently selected from nitrogen, oxygen and sulfur; and L is —C(=O)—, —O—C(=O)— or O—$C_{1-6}$alkyl-C(=O)—.

5. A compound according to claim 1, wherein $R_1$ is Het$^1$ or Het$^1C_{1-6}$alkyl; wherein said Het$^1$ comprises at least two heteroatoms each independently selected from nitrogen, oxygen and sulfur; and L is —C(=O)—, —O—C(=O)— or O—$C_{1-6}$alkanediyl-C(=O)—.

6. A compound according to claim 2, wherein, $R_1$ is 2-thiazolylmethyl-; and L is —O—C(=O)—.

7. A compound according to claim 1, wherein $R_1$ is Het$^1$ or Het$^1C_{1-6}$alkyl; wherein said Het$^1$ comprises at least one heteroatom independently selected from nitrogen, oxygen and sulfur; and L is O—$C_{1-6}$alkanediyl-C(=O)—.

8. A compound selected from the group consisting of:

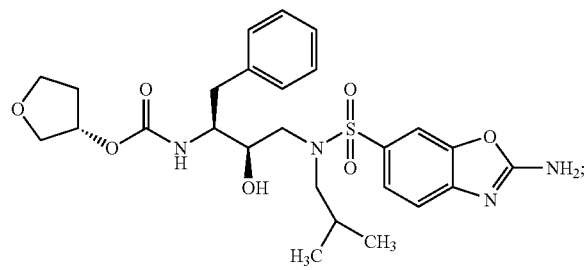

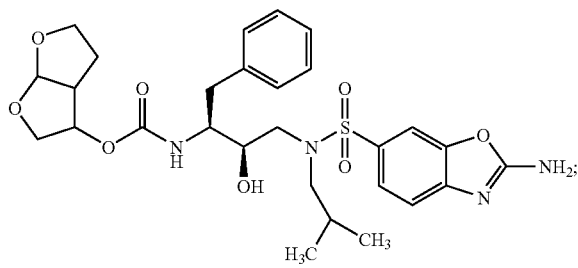

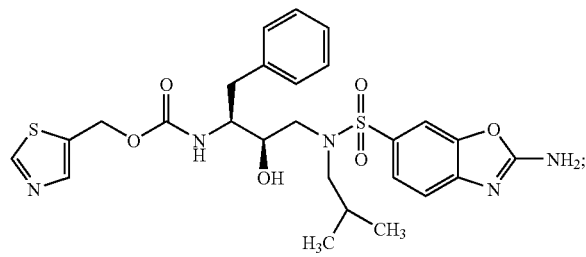

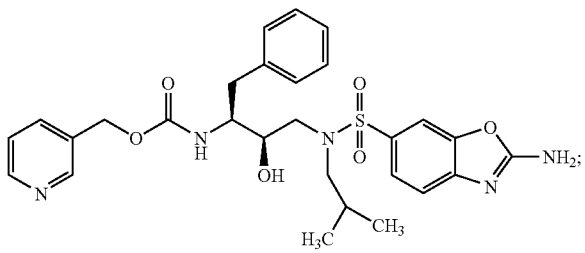

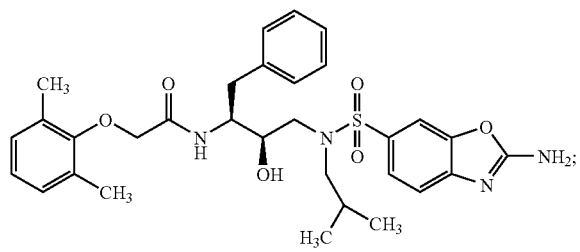

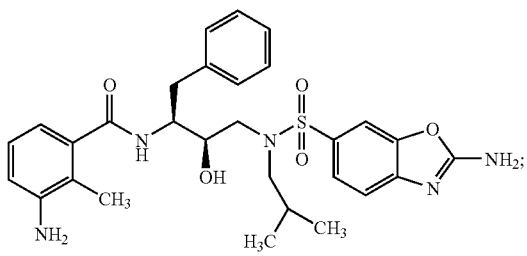

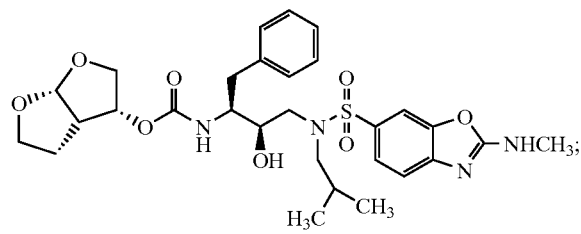

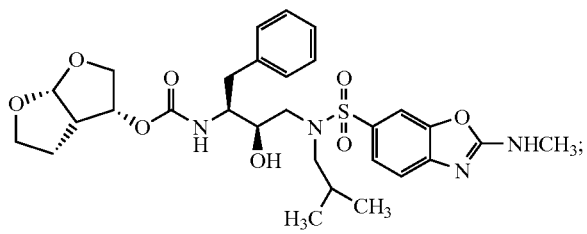

-continued
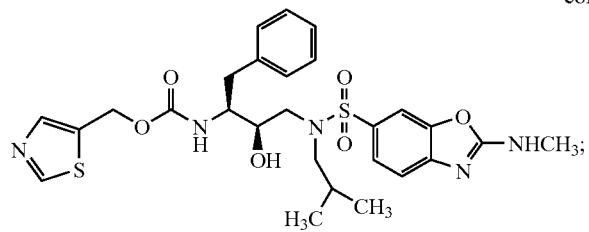
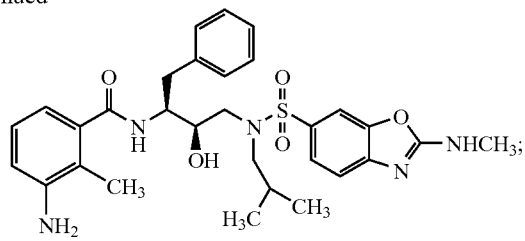
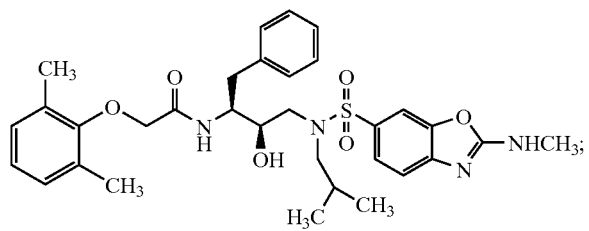
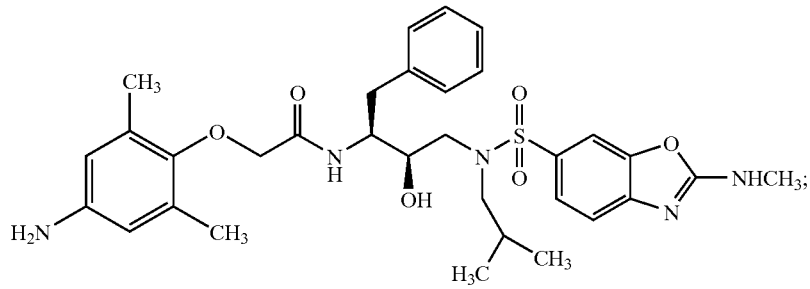
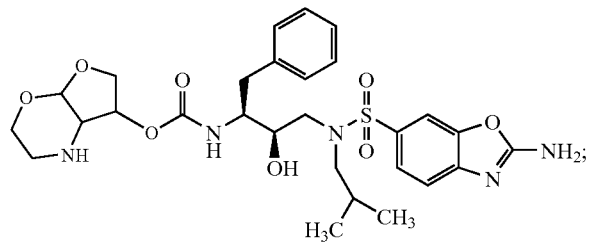
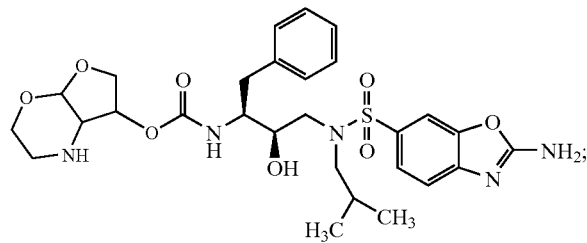
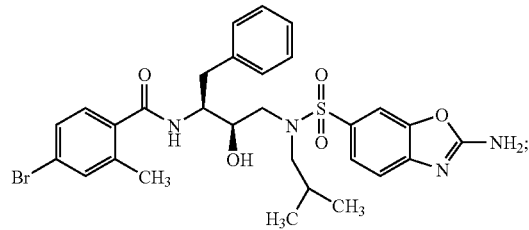
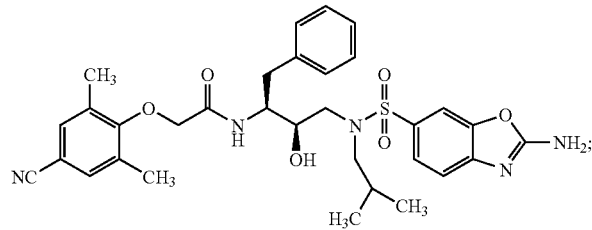
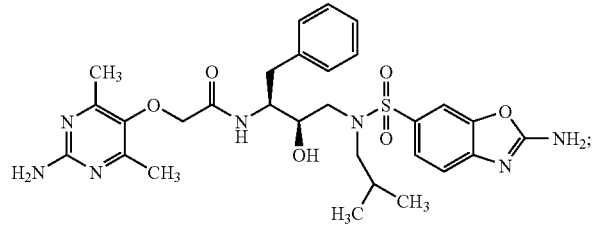
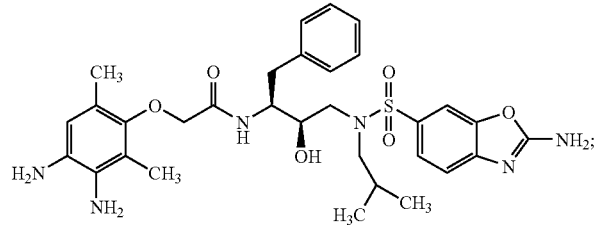
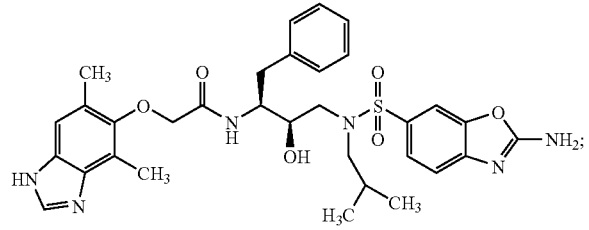
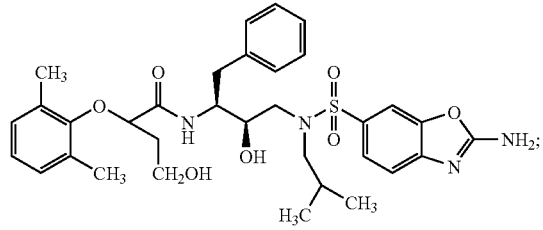

45 46
-continued
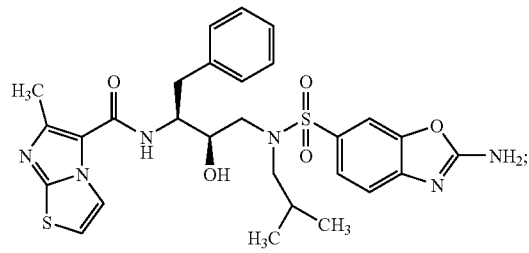
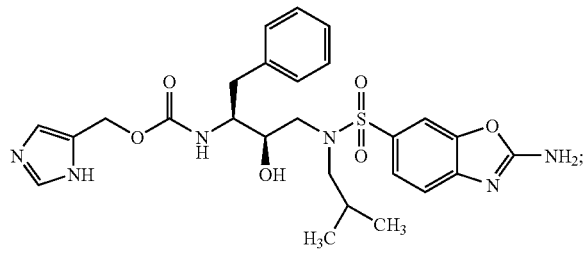
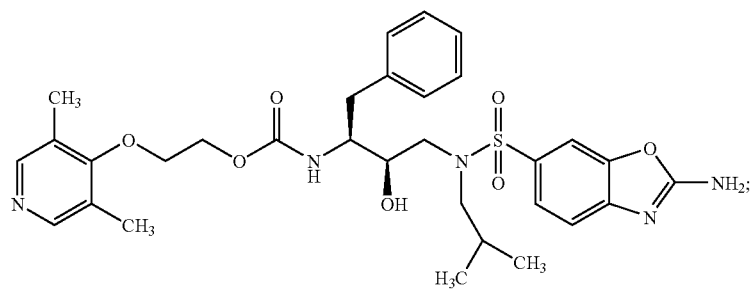
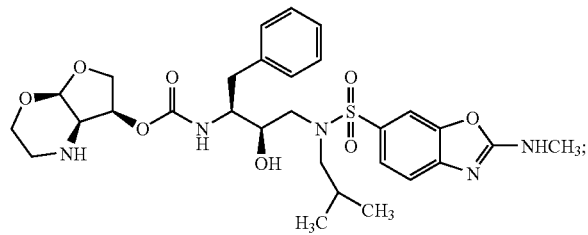
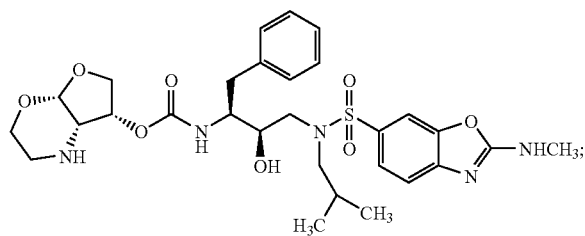
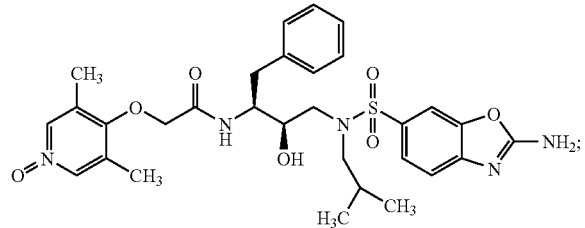
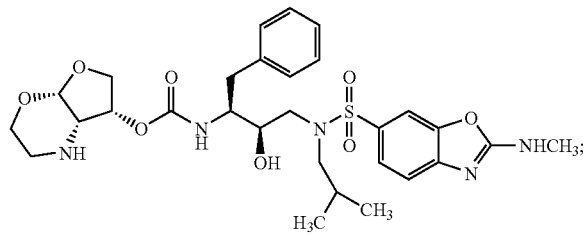
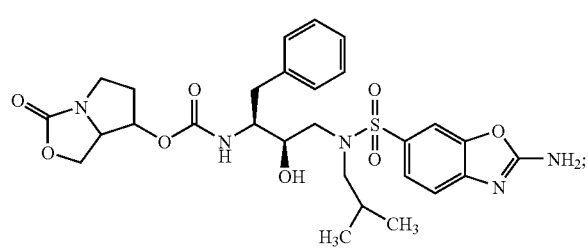
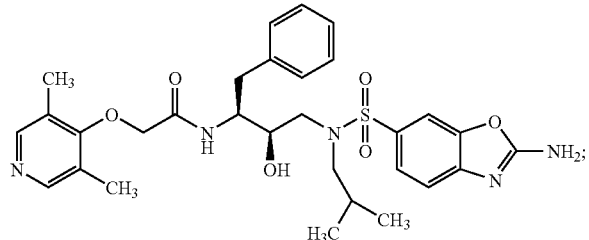
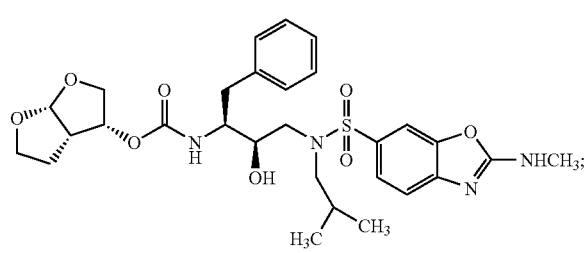

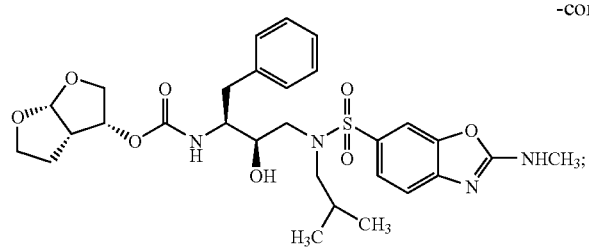
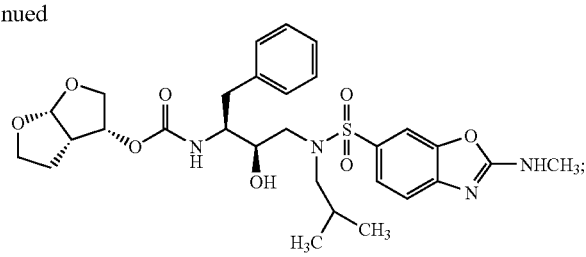
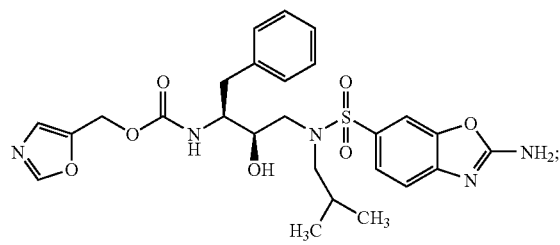
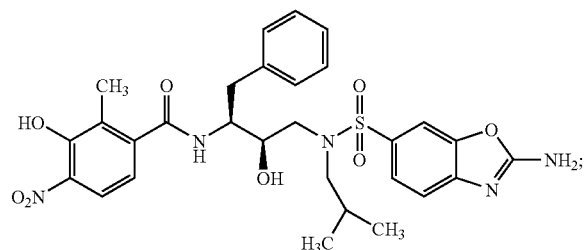
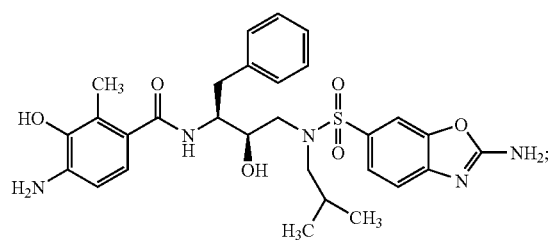
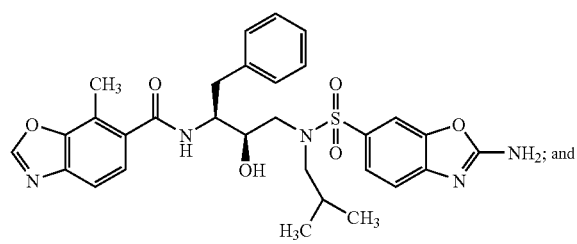
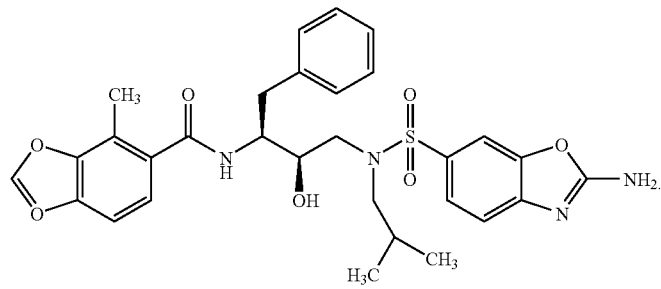
9. A compound having the structure:
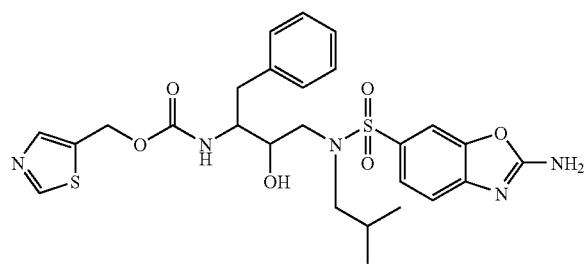
or an N-oxide, salt, stereoisomeric form, racemic mixture, prodrug, or ester thereof.
10. A compound having the structure:
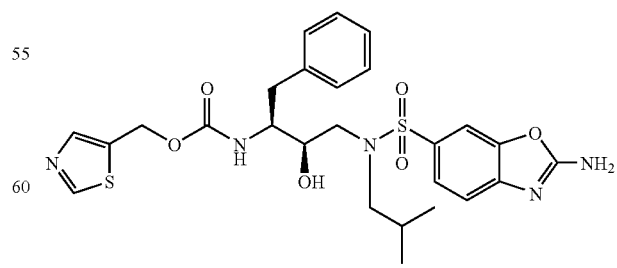
or an N-oxide, salt, stereoisomeric form, racemic mixture, prodrug, or ester thereof.

11. A compound having the structure:

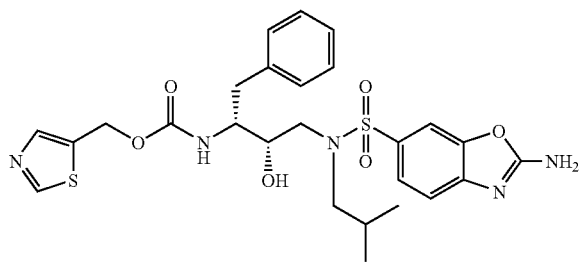

or an N-oxide, salt, stereoisomeric form, racemic mixture, prodrug, or ester thereof.

12. A compound having the structure as depicted in claim 9 wherein the compound is in its free base form.

13. A compound having the structure as depicted in claim 10 wherein the compound is in its free base form.

14. A compound having the structure as depicted in claim 11 wherein the compound is in its free base form.

15. A salt of the compound having the structure as depicted in claim 9.

16. A salt of the compound having the structure as depicted in claim 10.

17. An N-oxide form of the compound of claim 9.

18. An N-oxide form of the compound of claim 10.

19. An N-oxide form of the compound of claim 11.

20. A prodrug of the compound of claim 9.

21. A prodrug of the compound of claim 10.

22. A prodrug of the compound of claim 11.

23. A pharmaceutical composition, comprising an effective amount of at least one compound as claimed in claim 1, and a pharmaceutically tolerable excipient.

24. A pharmaceutical composition, comprising an effective amount of at least one compound as claimed in claim 1, and a modulator of the metabolization of said compound.

25. A pharmaceutical composition consisting of a solid dispersion comprising, (a) a compound as claimed in claim 1, and (b) one or more pharmaceutically acceptable water-soluble polymers.

26. A compound having the structure:

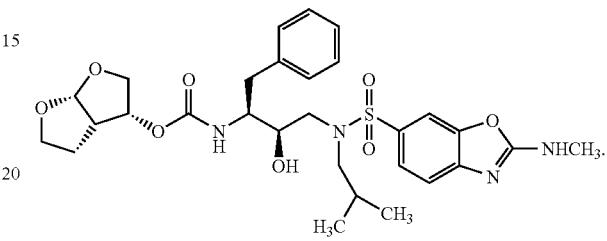

or an N-oxide, salt, stereoisomeric form, racemic mixture, prodrug, or ester thereof.

27. A compound having the structure as depicted in claim 26 wherein the compound is in its free base form.

28. A salt of the compound having the structure as depicted in claim 26.

* * * * *

UNITED STATES PATENT AND TRADEMARK OFFICE
CERTIFICATE OF CORRECTION

| | | |
|---|---|---|
| PATENT NO. | : 7,622,490 B2 | Page 1 of 1 |
| APPLICATION NO. | : 10/474485 | |
| DATED | : November 24, 2009 | |
| INVENTOR(S) | : Surleraux et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 326 days.

Signed and Sealed this

Fourteenth Day of December, 2010

David J. Kappos
*Director of the United States Patent and Trademark Office*